US012080432B1

(12) United States Patent
Johnson et al.

(10) Patent No.: US 12,080,432 B1
(45) Date of Patent: Sep. 3, 2024

(54) PLASMA METABOLOME AS A PREDICTOR OF BIOLOGICAL AGING

(71) Applicant: The Regents of the University of Colorado, Denver, CO (US)

(72) Inventors: Lawrence Cody Johnson, Broomfield, CO (US); Christopher R. Martens, Kennett Square, PA (US); Douglas R. Seals, Boulder, CO (US); Keli Parker, Ann Arbor, MI (US)

(73) Assignee: The Regents of the University of Colorado, Denver, CO (US)

( * ) Notice: Subject to any disclaimer, the term of this patent is extended or adjusted under 35 U.S.C. 154(b) by 1352 days.

(21) Appl. No.: 15/995,966

(22) Filed: Jun. 1, 2018

Related U.S. Application Data

(60) Provisional application No. 62/513,758, filed on Jun. 1, 2017.

(51) Int. Cl.
| | |
|---|---|
| *G01N 33/50* | (2006.01) |
| *G16B 20/00* | (2019.01) |
| *G16B 40/00* | (2019.01) |
| *G16H 50/20* | (2018.01) |
| *G16H 50/30* | (2018.01) |

(52) U.S. Cl.
CPC ......... *G16H 50/30* (2018.01); *G01N 33/5091* (2013.01); *G16B 20/00* (2019.02); *G16B 40/00* (2019.02); *G16H 50/20* (2018.01)

(58) Field of Classification Search
None
See application file for complete search history.

(56) References Cited

U.S. PATENT DOCUMENTS

| | | | |
|---|---|---|---|
| 7,781,160 | B2 | 8/2010 | Ryals et al. |
| 2003/0082597 | A1 | 5/2003 | Cannon et al. |
| 2008/0124752 | A1* | 5/2008 | Ryals ................. G01N 30/7233 436/63 |
| 2016/0116461 | A1 | 4/2016 | Ryals et al. |
| 2016/0169915 | A1 | 6/2016 | West et al. |

FOREIGN PATENT DOCUMENTS

| | | | |
|---|---|---|---|
| EP | 2813580 A1 | 12/2014 | |
| WO | WO-2014154494 A1 * | 10/2014 | ........... A61K 31/715 |

OTHER PUBLICATIONS

Fitzpatrick et al. (Swiss Med. Wkly (2015) vol. 143: 18 pages).*
Lum et al. (J. Gerontol. A Biol. Sci. Med. Sci. (2011) vol. 66A(5):548-553).*
Kuro-o (Mechanisms of Ageing and Development (2010) vol. 131: 270-275).*
Diaz-Ramos et al. (J. Biomedicine and Biotechnology (2012) Article ID 156795:12 pages).*
Lawton et al. (Pharmacogenomics (2008) vol. 9(4):383-397).*
Barallobre-Barreiro et al., Proteomics and Metabolomics for Mechanistic Insights and Biomarker Discovery in Cardiovascular Disease. Revista Española de Cardiologia (English Edition). 2013. vol. 66 (No. 8): 657-661.
Belsky et al., Quantification of biological aging in young adults. Proc Natl Acad Sci U S A. 2015. vol. 112: E4104-E4110.
Brooks-Wilson. Genetics of healthy aging and longevity. Hum Genet. 2013. vol. 132: 1323-1338.
Cho et al., An empirical comparative study on biological age estimation algorithms with an application of Work Ability Index (WAI). Mech Ageing Dev. 2010. vol. 131: 69-78.
Clasquin et al., LC-MS data processing with MAVEN: a metabolomic analysis and visualization engine. Curr Protoc Bioinformatics. 2012. Chapter 14: Unit 14.11, 31 pages.
Finkel. The metabolic regulation of aging. Nature medicine. 2015. vol. 21 (No. 12): 1416-1423.
Hannum et al., Genome-wide methylation profiles reveal quantitative views of human aging rates. Mol Cell.2013. vol. 49 (No. 2): 359-367.
Hardie et al., AMPK: a nutrient and energy sensor that maintains energy homeostasis. Nat Rev Mol Cell Biol. 2012. vol. 13 (No. 4): 251-262.
Horvath. DNA methylation age of human tissues and cell types. Genome Biol. 2013. vol. 14: R115, 20 pages.
Houtkooper et al., The metabolic footprint of aging in mice. Sci Rep. 2011. vol. 1: 134, 11 pages.
Houtkooper et al., Metabolic networks of longevity. Cell. 2010. vol. 142: 9-14.
Kennedy et al., Aging: a common driver of chronic diseases and a target for novel interventions. Cell. 2014. vol. 159 (No. 4): 709-713.
Kim et al., The frailty index outperforms DNA methylation age and its derivatives as an indicator of biological age. Geroscience. 2017. vol. 39: 83-92.

(Continued)

*Primary Examiner* — Lori A. Clow
(74) *Attorney, Agent, or Firm* — Michael M. McGaw; McGaw Law, P.C.

(57) ABSTRACT

Chronological age is an important predictor of morbidity and mortality, however it is unable to account for heterogeneity in the decline of physiological function and health with advancing age. Several attempts have been made to instead define a "biological age" using multiple physiological parameters in order to account for variation in the trajectory of human aging; however, these methods require technical expertise and are likely too time-intensive and costly to be implemented into clinical practice. Accordingly, a metabolomic signature of biological aging was developed that can predict changes in physiological function with the convenience of a blood sample. A weighted model of biological age was generated based on multiple clinical and physiological measures in a large group of healthy adults and was then applied to a cohort of healthy older adults who were tracked longitudinally over a 5-10 year timeframe. Plasma metabolomic signatures were identified that were associated with biological age, including some that could predict whether individuals would age at a faster or slower rate. These results not only have clinical implications by providing a simple blood-based assay of biological aging, but also provide insight into the molecular mechanisms underlying human healthspan.

1 Claim, 8 Drawing Sheets

(56) References Cited

OTHER PUBLICATIONS

Lawton et al., Analysis of the adult human plasma metabolome. Pharmacogenomics. 2008. vol. 9 (No. 4): 383-397.

Lopez-Otin et al., The hallmarks of aging. Cell. 2013. vol. 153 (No. 6): 1194-1217.

Lopez-Otin et al., Metabolic control of longevity. Cell. 2016. vol. 166: 802-821.

Mapstone et al., Plasma phospholipids identify antecedent memory impairment in older adults. Nature medicine. 2014. vol. 20 (No. 4): 415-418.

Noland et al., Carnitine insufficiency caused by aging and overnutrition compromises mitochondrial performance and metabolic control. Journal of Biological Chemistry. 2009. vol. 284 (No. 34): 22840-22852.

Sebastiani et al., Biomarker signatures of aging. Aging cell. 2017. vol. 16: 329-338.

Soltow et al., A network perspective on metabolism and aging. Integrative and comparative biology. 2010. vol. 50 (No. 5): 844-854.

Trushina et al., Identification of Altered Metabolic Pathways in Plasma and CSF in Mild Cognitive Impairment and Alzheimer's Disease Using Metabolomics. PLOS One. 2013. vol. 8 (No. 5): e63644, 13 pages.

Lustgarten et al., Metabolites related to gut bacterial metabolism, peroxisome proliferator-activated receptor-alpha activation, and insulin sensitivity are associated with physical function in functionally-limited older adults. Aging Cell. 2014. vol. 13: 918-925.

\* cited by examiner

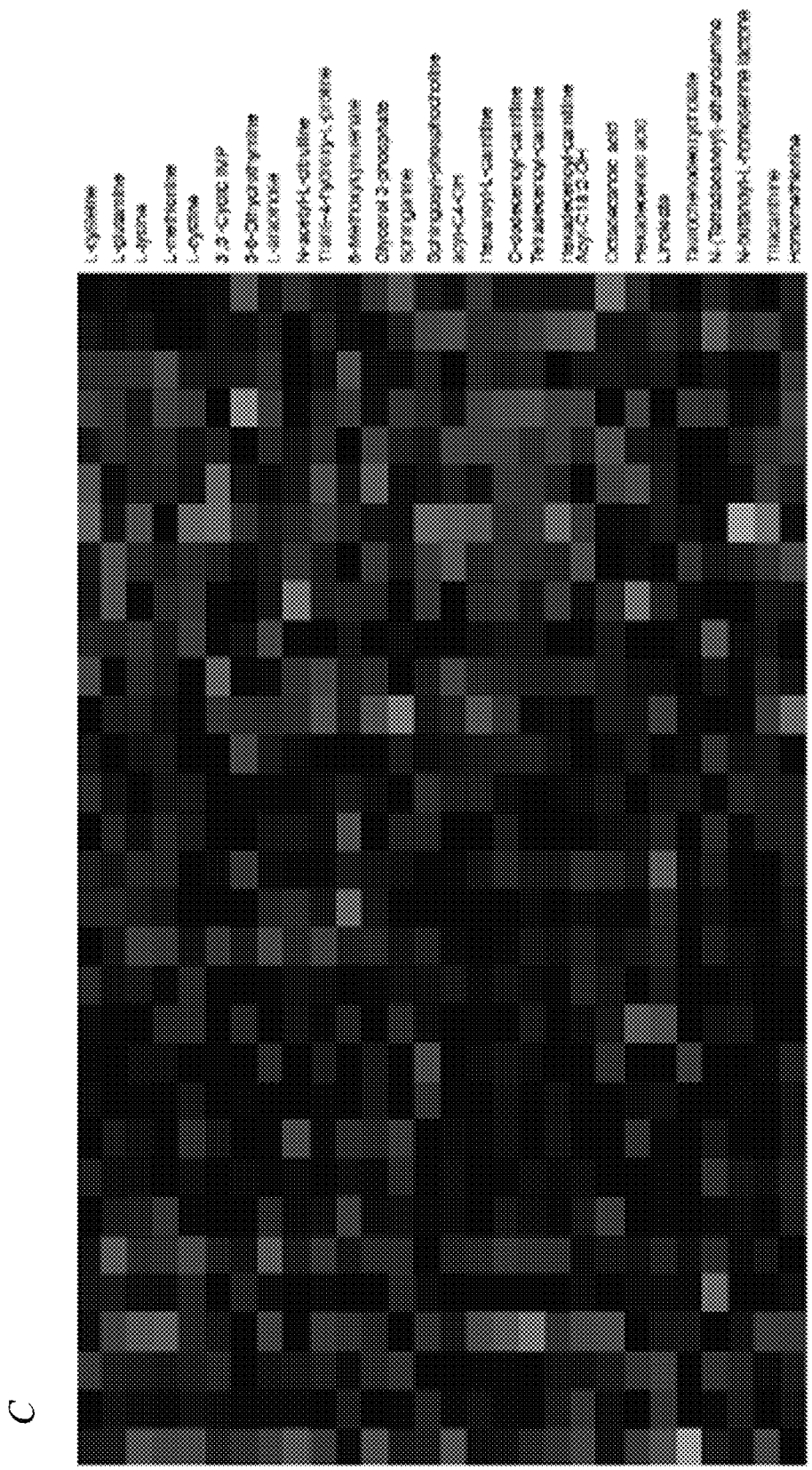
FIG. 4 - continued

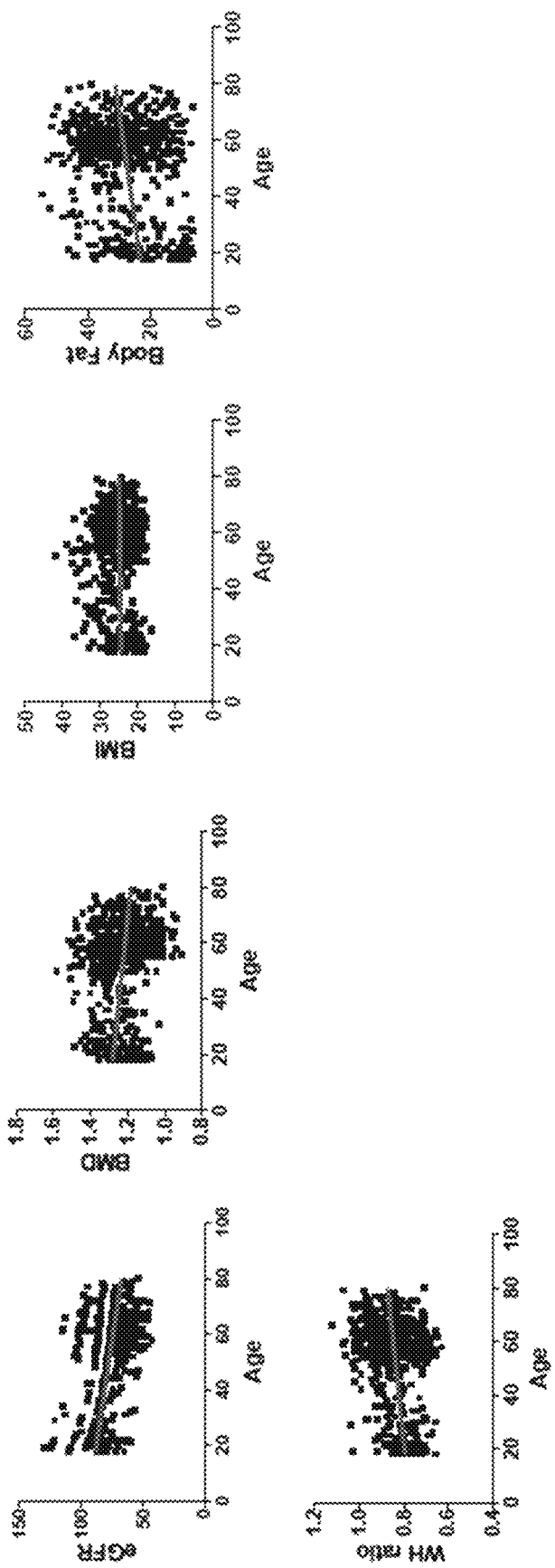
FIG. 5 - continued

PLASMA METABOLOME AS A PREDICTOR OF BIOLOGICAL AGING

CROSS-REFERENCE TO RELATED APPLICATIONS

This application claims the benefit of U.S. Provisional Application No. 62/513,758, filed Jun. 1, 2017.

STATEMENT OF GOVERNMENT INTEREST

This invention was made with government support under grant number AG013038 awarded by the National Institutes of Health. The government has certain rights in the invention.

BACKGROUND OF THE INVENTION

Advanced chronological age is one of the most important risk factors for many of the chronic diseases and disabilities affecting contemporary societies (Lunenfeld & Stratton 2013). The link between advancing age and increased chronic disease risk is predominately mediated by the progressive decline of multiple physiological systems (Franceschi & Campisi 2014; Kennedy et al. 2014). While aging itself is inescapable, the rate at which physiological functions decline with advancing age is highly variable among individuals and is the combined result of genetic and non-genetic factors including lifestyle behaviors (e.g., diet and physical activity) and other environmental or occupational exposures (e.g., sun damage or proximity to volatile chemicals) (Brooks-Wilson 2013; Jiang et al. 2013). As such, individuals of the same chronological age may differ considerably with respect to their physiological function and overall health status, thus limiting the predictive capacity of chronological age alone in in determining overall disease risk.

In order to address this issue, recent attempts have been made to define a "biological age" that is more reflective of the inherent heterogeneity of human aging than chronological age (Nakamura 1991; Cho et al. 2010; Levine 2013; Mitnitski et al. 2013; Belsky et al. 2015; Sebastiani et al. 2017). Central to this approach is the integration of multiple age-related "biomarkers" that are modifiable by lifestyle behaviors and other environmental exposures, and therefore more reflective of overall health than chronological age alone. Biological age, determined using clinical and physiological parameters, predicts morbidity and mortality better than chronological age alone (Levine 2013); however, the clinical utility of this approach is limited by the substantial cost, time, specialized equipment and training required to accurately assess multiple physiological functions. As such, the development of a surrogate blood-based measure of biological age would eliminate the burden of making multiple clinical and physiological assessments and more rapidly identify individuals at risk for faster aging and in need of appropriate interventions capable of modifying compromised physiological systems to reduce biological age. Moreover, such biomarkers may offer insight into the underlying mechanisms of aging and provide new targets for therapies aimed at improving human healthspan.

SUMMARY OF THE INVENTION

The metabolome, defined as all small molecules characterizing a biological system, is altered with age and reflective of age-related changes in physiological function (Lawton et al. 2008; Houtkooper et al. 2011; Mapstone et al. 2014).

Plasma metabolomic signatures were identified that are associated with biological aging in healthy adults. To do this, we trained a model of biological age based on clinical and physiological measures in a large cohort of healthy adults and tested it in a smaller cohort of mostly healthy middle-aged and older adults who were tracked longitudinally over a 5-10 year time frame. Small molecule signatures were identified that are present at baseline and/or follow-up in the longitudinal cohort that are associated with biological aging, including metabolites that are predictive of faster vs. slower aging, providing an opportunity for clinical actions to address the physiological variables contributing to an accelerated aging phenotype (i.e. therapeutics for elevated glucose or cholesterol profiles).

Chronological age is an important predictor of morbidity and mortality, however it is unable to account for heterogeneity in the decline of physiological function and health with advancing age. Several attempts have been made to instead define a "biological age" using multiple physiological parameters in order to account for variation in the trajectory of human aging; however, these methods require technical expertise and are likely too time-intensive and costly to be implemented into clinical practice. Accordingly, a metabolomic signature of biological aging was developed that can predict changes in physiological function with the convenience of a blood sample. A weighted model of biological age was generated based on multiple clinical and physiological measures in a large group of healthy adults and was then applied to a cohort of healthy older adults who were tracked longitudinally over a 5-10 year timeframe. Plasma metabolomic signatures were identified that were associated with biological age, including some that could predict whether individuals would age at a faster or slower rate. These results not only have clinical implications by providing a simple blood-based assay of biological aging, but also provide insight into the molecular mechanisms underlying human healthspan.

In a first aspect the present invention provides a method for metabolomically evaluating a subject's biological age. The method includes the steps of generating a small molecule profile from the subject using samples collected from the subject and comparing the levels of the small molecules of the subject to a known standard established for a population of subjects of about the same chronological age or age group using a plurality of small molecule metabolomic markers indicative of the biological age of the population of subjects. The metabolomic markers can be established by performing a plurality of physiologic, biologic and/or clinical tests on a population of subjects, where, advantageously, the subjects are of the same or similar chronologic age, gender, race, and/or ethnicity and, preferentially, their health status is known. Metabolomic analysis can then be performed on a sample taken from the subject. The sample is preferentially a blood or plasma sample, but numerous sources can be used to obtain a sample for metabolomic analysis including, saliva, urine, fecal matter, tissue and cells. Correlations can then be established between the presence, absence or level(s) of the metabolites in the population of subjects with the results of the physiologic, biologic and/or clinical tests, where the tests are indicative of the development of age-related disease or disability. Markers established in this manner can be further validated by confirming their presence, absence or level(s) in subjects with age-related disease or disability.

When performing metabolomic analysis of a sample, separation methods are usually paired with a detection method. Separation methods include gas chromatography, high performance liquid chromatography, ultra-high performance liquid chromatography, capillary electrophoresis. Detection methods include mass spectrometry, secondary ion mass spectrometry, nuclear magnetic resonance spectroscopy, ion mobility spectrometry, electrochemical detection, raman spectroscopy, radiolabel. Other methods can include spectrophotometry/colorimetry, transmittance, reflectometry, turbidimetry.

In an advantageous embodiment the plurality of small molecule metabolomic markers indicative of the biological age of subject comprises one or markers selected from the group consisting of N-(Tetradecanoyl)-ethanolamine, gamma-L-Glutamyl-Lcysteine, L-phenylalanine, L-aspartate, 5-Hydroxyisourate, 2-acyl-sn-glycero-3-phosphoethanolamine, ADP, Nicotinamide, 4-Nitroaniline, Salicylate, Felbamate, Pantetheine, 10-Hydroxydecanoic acid, Phenylgalactoside, 4-Hydroxybenzoate, Theogallin, and 6-Thioxanthine 5'-monophosphate.

Where one of the markers is N-(Tetradecanoyl)-ethanolamine, gamma-L-Glutamyl-Lcysteine, L-phenylalanine, L-aspartate, 5-Hydroxyisourate, 2-acyl-sn-glycero-3-phosphoethanolamine, ADP, Nicotinamide, 4-Nitroaniline, Salicylate, or Felbamate, and an increase in the marker is indicative an elevated biological age for the subject relative to the population of subjects of the same chronological age. Where one of the markers is Pantetheine, 10-Hydroxydecanoic acid, Phenylgalactoside, 4-Hydroxybenzoate, Theogallin, and 6-Thioxanthine 5'-monophosphate, and an increase in the marker is indicative of a reduced biological age for the subject relative to the population of subjects of the same chronological age.

In a second aspect the present invention provides a method for metabolomically evaluating a subject's expected future biological aging rate. The method includes the steps of generating a small molecule profile from the subject using samples collected from the subject and comparing the levels of the small molecules of the subject to a known standard established for a population of subjects of the same chronological age using a plurality of small molecule metabolomic markers indicative of future rate of aging of the population of subjects.

In an advantageous embodiment the plurality of small molecule metabolomic markers indicative of rate of aging of the population of subjects comprises one or markers selected from the group consisting of Oxalosuccinate, Oxaloacetate, 3',5'-Cyclic IMP, Phosphate, 2-Phospho-D-glycerate, Selenohomocystine, 4-Hydroxy-2',3,5,5'-tetrachlorobiphenyl, Geranyl diphosphate, 5-Acetylamino-6-formylamino-3-methyluracil, Nicotinamide, α-D-Glucosamine 1 phosphate, Glycochenodeoxycholate, Ethylenethiourea, and Octylamine. Where one of the markers is Oxalosuccinate or Oxaloacetate, an increase in the marker is indicative an elevated speed of aging in the future for the subject relative to the population of subjects of the same chronological age. Where the one of the markers is 3',5'-Cyclic IMP, Phosphate, 2-Phospho-D-glycerate, Selenohomocystine, 4-Hydroxy-2', 3,5,5'-tetrachlorobiphenyl, Geranyl diphosphate, 5-Acetylamino-6-formylamino-3-methyluracil, Nicotinamide, α-D-Glucosamine 1 phosphate, Glycochenodeoxycholate, Ethylenethiourea, or Octylamine, an increase in the marker is indicative an reduced speed of aging in the future for the subject relative to the population of subjects of the same chronological age.

In a third aspect the present invention provides a method for metabolomically evaluating a subject's current age rate. The method can include the steps of generating a small molecule profile from the subject using samples collected from the subject and comparing the levels of the small molecules of the subject to a known standard established for a population of subjects of the same chronological age using a plurality of small molecule metabolomic markers indicative of current rate of aging of the population of subjects.

In an advantageous embodiment the plurality of small molecule metabolomic markers indicative of current rate of aging of the population of subjects comprises one or markers selected from the group consisting of L-cysteine, acyl-C4-OH, L-glutamine, hexanoyl-L-carnitine, L-lysine, O-dodecenoyl-carnitine, L-methionine, Tetradecenoyl Carnitine, L-cystine, Hexadecenoyl-carnitine, 3',5'-Cyclic IMP, acyl-C18:2-OH, 5-6-Dihydrothymine, Octadecanoic acid, L-Arabinose, Hexadecenoic acid, N-Acetyl-L-citrulline, Linoleate, trans-4-Hydroxy-L-proline, Taurochenodeoxycholate, 8-Methoxykynurenate, N-(Tetradecanoyl)-ethanolamine, Glycerol 3-phosphate, N-butanoyl-lhomoserine lactone, Sphinganine, Triacanthine, Sphingosyl-phosphocholine, and Homomethionine. Where one of the markers is L-cysteine, acyl-C4-OH, L-glutamine, hexanoyl-L-carnitine, L-lysine, O-dodecenoyl-carnitine, L-methionine, Tetradecenoyl Carnitine, L-cystine, Hexadecenoyl-carnitine, 3',5'-Cyclic IMP, acyl-C18:2-OH, 5-6-Dihydrothymine, Octadecanoic acid, L-Arabinose, Hexadecenoic acid, N-Acetyl-L-citrulline, Linoleate, trans-4-Hydroxy-L-proline, Taurochenodeoxycholate, 8-Methoxykynurenate, N-(Tetradecanoyl)-ethanolamine, Glycerol 3-phosphate, N-butanoyl-lhomoserine lactone, Sphinganine, Triacanthine, Sphingosyl-phosphocholine, or Homomethionine, an increase in the marker is indicative an increased speed of aging in the future for the subject relative to the population of subjects of the same chronological age.

In a fourth aspect the present invention provides a method for screening the metabolome of a subject for alterations in the levels of metabolites associated with aging. The method can include the steps of generating a small molecule profile from the subject using samples collected from the subject and comparing the small molecule profile of the subject to a known standard established for a population of subjects of the same chronological age using a plurality of metabolomics markers indicative of the biological age of the population. In an advantageous embodiment the sample is a blood or plasma sample.

In a fifth aspect the present invention provides a method for metabolomically evaluating a subject's biological age and can comprise performing the methods of any of the first three aspects in combination. In an advantageous embodiment a single plasma sample is used to perform the method of any of the aspects listed herein for metabolomically evaluating a subject's biological age.

In a sixth aspect the present invention provides a method of screening for the presence, absence or level(s) of one or more metabolites in a subject. The method includes the steps of obtaining a blood or plasma sample from the subject and generating a small molecule profile of metabolites from the blood or plasma sample obtained from the subject. The presence, absence or level(s) of one or more metabolites in the generated small molecule profile can be evaluated against a reference level for the one or more metabolites in a reference profile established by correlating the metabolites with a plurality of clinical, biological or physiological tests that are indicative of risk for the current or future development of age-related disease or disability.

In an advantageous embodiment, the step of generating a small molecule profile of metabolites from the blood or plasma sample obtained from the subject, as in the sixth aspect, can include performing liquid chromatography-mass spectrometry on the extracted sample to screen for the presence, absence or level(s) of one or metabolites including 6-Lactoyl-5-6-7-8-tetrahydropterin, Phaseolic acid, Anandamide, L-Homocitrulline, 4-Nitroaniline, Felbamate, 10-Hydroxydecanoic acid, Inositol 1-2-3-5-6-pentakisphosphate, Citrate, acyl-C18:2-OH, Phosphoserine, 1stgna-4-9(11)-diene-3-20-dione, Indole-3-acetate, 4-Hydroxybenzoate, Tetradecenoyl Carnitine, O-Dodecenoyl-carnitine, O-Decenoyl-L-carnitine, Putrescine, 6-Thioxanthine 5-monophosphate, Theogallin, Pantetheine, and combinations thereof.

In further advantageous embodiments, the subject can be screened for the presence, absence or level(s) of two or more metabolites. In certain embodiments two of the two or more metabolites can be (1) 6-Lactoyl-5-6-7-8-tetrahydropterin and Phaseolic acid, (2) 6-Lactoyl-5-6-7-8-tetrahydropterin and Anandamide, (3) 6-Lactoyl-5-6-7-8-tetrahydropterin and L-Homocitrulline, (4) 6-Lactoyl-5-6-7-8-tetrahydropterin and 4-Nitroaniline, 6-Lactoyl-5-6-7-8-tetrahydropterin and Felbamate, (5) Phaseolic acid and Anandamide, (6) Phaseolic acid and L-Homocitrulline, (7) Phaseolic acid and 4-Nitroaniline, (8) Phaseolic acid and Felbamate, (9) Anandamide and L-Homocitrulline, (10) Anandamide and 4-Nitroaniline, (11) Anandamide and Felbamate, (12) L-Homocitrulline and 4-Nitroaniline, (13) L-Homocitrulline and Felbamate, or (14) 4-Nitroaniline and Felbamate.

Alternatively, two of the two or more metabolites can be 10-Hydroxydecanoic acid and Inositol 1-2-3-5-6-pentakisphosphate, 10-Hydroxydecanoic acid and Citrate, 10-Hydroxydecanoic acid and acyl-C18:2-OH, 10-Hydroxydecanoic acid and Phosphoserine, 10-Hydroxydecanoic acid and 1stgna-4-9(11)-diene-3-20-dione, Indole-3-acetate, 10-Hydroxydecanoic acid and 4-Hydroxybenzoate, 10-Hydroxydecanoic acid and Tetradecenoyl Carnitine, 10-Hydroxydecanoic acid and O-Dodecenoyl-carnitine, 10-Hydroxydecanoic acid and O-Decenoyl-L-carnitine, 10-Hydroxydecanoic acid and Putrescine, 10-Hydroxydecanoic acid and 6-Thioxanthine 5-monophosphate, 10-Hydroxydecanoic acid and Theogallin, 10-Hydroxydecanoic acid and Pantetheine, Inositol 1-2-3-5-6-pentakisphosphate and Citrate, Inositol 1-2-3-5-6-pentakisphosphate and acyl-C18:2-OH, Inositol 1-2-3-5-6-pentakisphosphate and Phosphoserine, Inositol 1-2-3-5-6-pentakisphosphate and 1stgna-4-9(11)-diene-3-20-dione, Inositol 1-2-3-5-6-pentakisphosphate and Indole-3-acetate, Inositol 1-2-3-5-6-pentakisphosphate and 4-Hydroxybenzoate, Inositol 1-2-3-5-6-pentakisphosphate and Tetradecenoyl Carnitine, Inositol 1-2-3-5-6-pentakisphosphate and O-Dodecenoyl-carnitine, Inositol 1-2-3-5-6-pentakisphosphate and O-Decenoyl-L-carnitine, Inositol 1-2-3-5-6-pentakisphosphate and Putrescine, Inositol 1-2-3-5-6-pentakisphosphate and 6-Thioxanthine 5-monophosphate, Inositol 1-2-3-5-6-pentakisphosphate and Theogallin, Inositol 1-2-3-5-6-pentakisphosphate and Pantetheine, Citrate and acyl-C18:2-OH, Citrate and Phosphoserine, Citrate and 1stgna-4-9(11)-diene-3-20-dione, Citrate and Indole-3-acetate, Citrate and 4-Hydroxybenzoate, Citrate and Tetradecenoyl Carnitine, Citrate and O-Dodecenoyl-carnitine, Citrate and O-Decenoyl-L-carnitine, Citrate and Putrescine, Citrate and 6-Thioxanthine 5-monophosphate, Citrate and Theogallin, Citrate and Pantetheine, acyl-C18:2-OH and Phosphoserine, acyl-C18:2-OH and 1stgna-4-9(11)-diene-3-20-dione, acyl-C18:2-OH and Indole-3-acetate, acyl-C18:2-OH and 4-Hydroxybenzoate, acyl-C18:2-OH and Tetradecenoyl Carnitine, acyl-C18:2-OH and O-Dodecenoyl-carnitine, acyl-C18:2-OH and O-Decenoyl-L-carnitine, acyl-C18:2-OH and Putrescine, acyl-C18:2-OH and 6-Thioxanthine 5-monophosphate, acyl-C18:2-OH and Theogallin, acyl-C18:2-OH and Pantetheine, Phosphoserine and 1stgna-4-9(11)-diene-3-20-dione, Phosphoserine and Indole-3-acetate, Phosphoserine and 4-Hydroxybenzoate, Phosphoserine and Tetradecenoyl Carnitine, Phosphoserine and O-Dodecenoyl-carnitine, Phosphoserine and O-Decenoyl-L-carnitine, Phosphoserine and Putrescine, Phosphoserine and 6-Thioxanthine 5-monophosphate, Phosphoserine and Theogallin, Phosphoserine and Pantetheine, 1stgna-4-9(11)-diene-3-20-dione and Indole-3-acetate, 1stgna-4-9(11)-diene-3-20-dione and 4-Hydroxybenzoate, 1stgna-4-9(11)-diene-3-20-dione and Tetradecenoyl Carnitine, 1stgna-4-9(11)-diene-3-20-dione and O-Dodecenoyl-carnitine, 1stgna-4-9(11)-diene-3-20-dione and O-Decenoyl-L-carnitine, 1stgna-4-9(11)-diene-3-20-dione and Putrescine, 1stgna-4-9(11)-diene-3-20-dione and 6-Thioxanthine 5-monophosphate, 1stgna-4-9(11)-diene-3-20-dione and Theogallin, 1stgna-4-9(11)-diene-3-20-dione and Pantetheine, Indole-3-acetate and 4-Hydroxybenzoate, Indole-3-acetate and Tetradecenoyl Carnitine, Indole-3-acetate and O-Dodecenoyl-carnitine, Indole-3-acetate and O-Decenoyl-L-carnitine, Indole-3-acetate and Putrescine, Indole-3-acetate and 6-Thioxanthine 5-monophosphate, Indole-3-acetate and Theogallin, Indole-3-acetate and Pantetheine, 4-Hydroxybenzoate and Tetradecenoyl Carnitine, 4-Hydroxybenzoate and O-Dodecenoyl-carnitine, 4-Hydroxybenzoate and O-Decenoyl-L-carnitine, 4-Hydroxybenzoate and Putrescine, 4-Hydroxybenzoate and 6-Thioxanthine 5-monophosphate, 4-Hydroxybenzoate and Theogallin, 4-Hydroxybenzoate and Pantetheine, Tetradecenoyl Carnitine and O-Dodecenoyl-carnitine, Tetradecenoyl Carnitine and O-Decenoyl-L-carnitine, Tetradecenoyl Carnitine and Putrescine, Tetradecenoyl Carnitine and 6-Thioxanthine 5-monophosphate, Tetradecenoyl Carnitine and Theogallin, Tetradecenoyl Carnitine and Pantetheine, O-Dodecenoyl-carnitine and O-Decenoyl-L-carnitine, O-Dodecenoyl-carnitine and Putrescine, O-Dodecenoyl-carnitine and 6-Thioxanthine 5-monophosphate, O-Dodecenoyl-carnitine and Theogallin, O-Dodecenoyl-carnitine and Pantetheine, O-Decenoyl-L-carnitine and Putrescine, O-Decenoyl-L-carnitine and 6-Thioxanthine 5-monophosphate, O-Decenoyl-L-carnitine and Theogallin, O-Decenoyl-L-carnitine and Pantetheine, Putrescine and 6-Thioxanthine 5-monophosphate, Putrescine and Theogallin, Putrescine and Pantetheine, 6-Thioxanthine 5-monophosphate and Theogallin, 6-Thioxanthine 5-monophosphate and Pantetheine, or Theogallin and Pantetheine.

In further advantageous embodiments, in the method of the sixth aspect the subject can be screened for the presence, absence or level(s) of three or more metabolites. Three of the three or more metabolites can be (1) 6-Lactoyl-5-6-7-8-tetrahydropterin, Phaseolic acid and Anandamide, (2) 6-Lactoyl-5-6-7-8-tetrahydropterin, Phaseolic acid and L-Homocitrulline, (3) 6-Lactoyl-5-6-7-8-tetrahydropterin, Phaseolic acid and 4-Nitroaniline, (4) 6-Lactoyl-5-6-7-8-tetrahydropterin, Phaseolic acid and Felbamate, (5) Phaseolic acid, Anandamide, and L-Homocitrulline, (6) Phaseolic acid, Anandamide, and 4-Nitroaniline, (7) Phaseolic acid, Anandamide, and Felbamate, (8) Anandamide, L-Homocitrulline, and 4-Nitroaniline, (9) Anandamide, L-Homocitrulline, and Felbamate, or (10) L-Homocitrulline, 4-Nitroaniline, and Felbamate.

In still further advantageous embodiments of the method of the sixth aspect one of the one or more metabolites can be 6-Lactoyl-5-6-7-8-tetrahydropterin, Phaseolic acid, Anandamide, L-Homocitrulline, 4-Nitroaniline, or Felbamate. An elevated level of those metabolites in the subject relative to a population of subjects of the same or similar chronological age is indicative of a higher biological age of the subject relative to the population of subjects.

In still further advantageous embodiments of the method of the sixth aspect one of the one or more metabolites can be 10-Hydroxydecanoic acid, Inositol 1-2-3-5-6-pentakisphosphate, Citrate, acyl-C18:2-OH, Phosphoserine, 1stgna-4-9(11)-diene-3-20-dione, Indole-3-acetate, 4-Hydroxybenzoate, Tetradecenoyl Carnitine, O-Dodecenoyl-carnitine, O-Decenoyl-L-carnitine, Putrescine, 6-Thioxanthine 5-monophosphate, Theogallin, or Pantetheine. An elevated level of those metabolites in the subject relative to a population of subjects of the same or similar chronological age is indicative of a lower biological age of the subject relative to the population of subjects.

In still further advantageous embodiments of the method of the sixth aspect the subject is screened for the presence, absence or level(s) of four or more metabolites.

In still further advantageous embodiments of the method of the sixth aspect the subject is screened for the presence, absence or level(s) of five or more metabolites.

In an advantageous embodiment the step of generating a small molecule profile of metabolites from the blood or plasma sample obtained from the subject comprises performing liquid chromatography-mass spectrometry on the extracted sample to screen for the presence, absence or level(s) of one or metabolites comprising Oxaloacetate, Acyl-C5-OH, 2-Phospho-D-Glycerate, Ascorbate, Selenohomocystine, 5-Acetylamino-6-formylamino-3-methyluracil, Phosphate, and Octylamine.

In further advantageous embodiments of the sixth aspect the two or more metabolites are selected from the group consisting of Oxaloacetate and Acyl-C5-OH, Oxaloacetate and 2-Phospho-D-Glycerate, Oxaloacetate and Ascorbate, Oxaloacetate and Selenohomocystine, Oxaloacetate and 5-Acetylamino-6-formylamino-3-methyluracil, Oxaloacetate and Phosphate, Oxaloacetate and Octylamine, Acyl-C5-OH and 2-Phospho-D-Glycerate, Acyl-C5-OH and Ascorbate, Acyl-C5-OH and Selenohomocystine, Acyl-C5-OH and 5-Acetylamino-6-formylamino-3-methyluracil, Acyl-C5-OH and Phosphate, Acyl-C5-OH and Octylamine, 2-Phospho-D-Glycerate and Ascorbate, 2-Phospho-D-Glycerate and Selenohomocystine, 2-Phospho-D-Glycerate and 5-Acetylamino-6-formylamino-3-methyluracil, 2-Phospho-D-Glycerate and Phosphate, 2-Phospho-D-Glycerate and Octylamine, Ascorbate and Selenohomocystine, Ascorbate and Selenohomocystine, Ascorbate and 5-Acetylamino-6-formylamino-3-methyluracil, Ascorbate and Phosphate, Ascorbate and Octylamine, Selenohomocystine and 5-Acetylamino-6-formylamino-3-methyluracil, Selenohomocystine and Phosphate, Selenohomocystine and Octylamine, 5-Acetylamino-6-formylamino-3-methyluracil and Phosphate, 5-Acetylamino-6-formylamino-3-methyluracil and Octylamine, and Phosphate and Octylamine.

In still further advantageous embodiments of the sixth aspect three of the three or more metabolites are selected from the group consisting of (1) Oxaloacetate, Acyl-C5-OH, and 2-Phospho-D-Glycerate, (2) Oxaloacetate, Acyl-C5-OH, and Ascorbate, (3) Oxaloacetate, Acyl-C5-OH, and Selenohomocystine, (4) Oxaloacetate, Acyl-C5-OH, and 5-Acetylamino-6-formylamino-3-methyluracil, (5) Oxaloacetate, Acyl-C5-OH, and Phosphate, (6) Oxaloacetate, Acyl-C5-OH, and Octylamine, (7) Acyl-C5-OH, 2-Phospho-D-Glycerate, and Ascorbate, (8) Acyl-C5-OH, 2-Phospho-D-Glycerate, and Selenohomocystine, (9) Acyl-C5-OH, 2-Phospho-D-Glycerate, and 5-Acetylamino-6-formylamino-3-methyluracil, (10) Acyl-C5-OH, 2-Phospho-D-Glycerate, and Phosphate, (11) Acyl-C5-OH, 2-Phospho-D-Glycerate, and Octylamine, (12) 2-Phospho-D-Glycerate, Ascorbate, and Selenohomocystine, (13) 2-Phospho-D-Glycerate, Ascorbate, and 5-Acetylamino-6-formylamino-3-methyluracil, (14) 2-Phospho-D-Glycerate, Ascorbate, and Phosphate, (15) 2-Phospho-D-Glycerate, Ascorbate, and Octylamine, (16) Ascorbate, Selenohomocystine, and 5-Acetylamino-6-formylamino-3-methyluracil, (17) Ascorbate, Selenohomocystine, and Phosphate, (18) Ascorbate, Selenohomocystine, and Octylamine, (19) Selenohomocystine, 5-Acetylamino-6-formylamino-3-methyluracil, and Phosphate, (20) 5-Acetylamino-6-formylamino-3-methyluracil, and Octylamine, and (21) 5-Acetylamino-6-formylamino-3-methyluracil, Phosphate, and Octylamine.

In an advantageous embodiment of the sixth aspect one of the one or more metabolites can be Oxaloacetate or Acyl-C5-OH. An elevated level of those two metabolites in the subject relative to a population of subjects of the same or similar chronological age is indicative of faster future biological aging of the subject relative to the population of subjects.

In a further advantageous embodiment of the sixth aspect one of the one or more metabolites can be 2-Phospho-D-Glycerate, Ascorbate, Selenohomocystine, 5-Acetylamino-6-formylamino-3-methyluracil, Phosphate, or Octylamine. An elevated level of those metabolite in the subject relative to a population of subjects of the same or similar chronological age is indicative of slower future biological aging of the subject relative to the population of subjects.

In a seventh aspect the present invention provides a method of screening for the presence, absence or level(s) of one or more metabolites in a subject. The method of the seventh aspect can include the steps of obtaining a blood or plasma sample from the subject, extracting small molecule metabolites from the blood or plasma sample, and performing liquid chromatography-mass spectrometry on the extracted sample to screen for the presence, absence or level(s) of one or metabolites comprising Oxaloacetate, Acyl-C5-OH, 2-Phospho-D-Glycerate, Ascorbate, Selenohomocystine, 5-Acetylamino-6-formylamino-3-methyluracil, Phosphate, and Octylamine.

In an advantageous embodiment of the seventh aspect the subject is screened for the presence, absence or level(s) of two or more metabolites. The two or more metabolites can be Oxaloacetate and Acyl-C5-OH, Oxaloacetate and 2-Phospho-D-Glycerate, Oxaloacetate and Ascorbate, Oxaloacetate and Selenohomocystine, Oxaloacetate and 5-Acetylamino-6-formylamino-3-methyluracil, Oxaloacetate and Phosphate, Oxaloacetate and Octylamine, Acyl-C5-OH and 2-Phospho-D-Glycerate, Acyl-C5-OH and Ascorbate, Acyl-C5-OH and Selenohomocystine, Acyl-C5-OH and 5-Acetylamino-6-formylamino-3-methyluracil, Acyl-C5-OH and Phosphate, Acyl-C5-OH and Octylamine, 2-Phospho-D-Glycerate and Ascorbate, 2-Phospho-D-Glycerate and Selenohomocystine, 2-Phospho-D-Glycerate and 5-Acetylamino-6-formylamino-3-methyluracil, 2-Phospho-D-Glycerate and Phosphate, 2-Phospho-D-Glycerate and Octylamine, Ascorbate and Selenohomocystine, Ascorbate and Selenohomocystine, Ascorbate and 5-Acetylamino-6-formylamino-3-methyluracil, Ascorbate and Phosphate, Ascorbate and Octylamine, Selenohomocystine and 5-Acetylamino-6-formylamino-3-methyluracil, Selenohomocystine and Phosphate, Selenohomocystine and Octylamine, 5-Acetylamino-6-formylamino-3-methyluracil and Phosphate, 5-Acetylamino-6-formylamino-3-methyluracil and Octylamine, or Phosphate and Octylamine.

In further advantageous embodiments of the seventh aspect the subject is screened for the presence, absence or level(s) of three or more metabolites. Three of the three or more metabolites can be (1) Oxaloacetate, Acyl-C5-OH, and 2-Phospho-D-Glycerate, (2) Oxaloacetate, Acyl-C5-OH, and Ascorbate, (3) Oxaloacetate, Acyl-C5-OH, and Selenohomocystine, (4) Oxaloacetate, Acyl-C5-OH, and 5-Acetylamino-6-formylamino-3-methyluracil, (5) Oxaloacetate, Acyl-C5-OH, and Phosphate, (6) Oxaloacetate, Acyl-C5-OH, and Octylamine, (7) Acyl-C5-OH, 2-Phospho-D-Glycerate, and Ascorbate, (8) Acyl-C5-OH, 2-Phospho-D-Glycerate, and Selenohomocystine, (9) Acyl-C5-OH, 2-Phospho-D-Glycerate, and 5-Acetylamino-6-formylamino-3-methyluracil, (10) Acyl-C5-OH, 2-Phospho-D-Glycerate, and Phosphate, (11) Acyl-C5-OH, 2-Phospho-D-Glycerate, and Octylamine, (12) 2-Phospho-D-Glycerate, Ascorbate, and Selenohomocystine, (13) 2-Phospho-D-Glycerate, Ascorbate, and 5-Acetylamino-6-formylamino-3-methyluracil, (14) 2-Phospho-D-Glycerate, Ascorbate, and Phosphate, (15) 2-Phospho-D-Glycerate, Ascorbate, and Octylamine, (16) Ascorbate, Selenohomocystine, and 5-Acetylamino-6-formylamino-3-methyluracil, (17) Ascorbate, Selenohomocystine, and Phosphate, (18) Ascorbate, Selenohomocystine, and Octylamine, (19) Selenohomocystine, 5-Acetylamino-6-formylamino-3-methyluracil, and Phosphate, (20) 5-Acetylamino-6-formylamino-3-methyluracil, and Octylamine, or (21) 5-Acetylamino-6-formylamino-3-methyluracil, Phosphate, and Octylamine.

In an advantageous embodiment of the seventh aspect one of the one or more metabolites is Oxaloacetate or Acyl-C5-OH. An elevated level of those metabolites in the subject relative to a population of subjects of the same or similar chronological age is indicative of faster future biological aging of the subject relative to the population of subjects.

In another advantageous embodiment of the seventh aspect one of the one or more metabolites is 2-Phospho-D-Glycerate, Ascorbate, Selenohomocystine, 5-Acetylamino-6-formylamino-3-methyluracil, Phosphate, or Octylamine. An elevated level of those metabolites in the subject relative to a population of subjects of the same or similar chronological age is indicative of slower future biological aging of the subject relative to the population of subjects.

In an eighth aspect the present invention provides a method for identifying metabolites indicative of a subject's biological age. The method can include the steps of performing a plurality of biological, clinical and physiological tests on a population of subjects, wherein the clinical and physiological tests are indicative of risk for age-related disease or disability, generating a small molecule profile from each of the subjects in the population of subjects using samples collected from each subject in the population of subjects, and identifying small molecules associated with a subject's biological age by comparing the generated small molecule profiles to the results of the tests indicating subjects at risk for developing age-related disease based upon the results of the clinical and physiological tests.

In an advantageous embodiment the plurality of clinical and physiological tests are selected from the group consisting of Body Mass Index, Waist-to-Hip Ratio, Body Fat (%), Bone Mineral Density, Systolic Blood Pressure, Diastolic Blood Pressure, Glucose, Total Cholesterol, LDL-C, HDL-C, eGFR, Max Heart Rate, and VO$_2$max.

In an eighth aspect the present invention provides a method for identifying metabolites indicative of a subject's future rate of biological aging. The method of the eighth aspect includes the steps of performing a plurality of clinical and physiological tests on a population of subjects, wherein the clinical and physiological tests are indicative of risk for age-related disease and disability, generating a small molecule profile from each of the subjects in the population of subjects using samples collected from each subject in the population of subjects, repeating the performing and generating steps at a subsequent timepoint for each of the subjects in the population of subjects, and identifying changes in small molecule levels associated with a subject's future biological aging by comparing the generated small molecule profiles at the timepoints to the changes over the timepoints in the results of the tests indicating subjects at risk for developing age-related disease based upon the results of the clinical and physiological tests.

The subsequent timepoints can be about one week, about one month, about three months, about six months, about nine months, about one year, about two years, about three years, about four years, about five years, about six years, and about ten years following a baseline test. It is further contemplated that there can be a plurality of subsequent tests, such as at the timepoints listed above.

In an advantageous embodiment one of the plurality of clinical and physiological tests are selected from the group consisting of Body Mass Index, Waist-to-Hip Ratio, Body Fat (%), Bone Mineral Density, Systolic Blood Pressure, Diastolic Blood Pressure, Glucose, Total Cholesterol, LDL-C, HDL-C, eGFR, Max Heart Rate, and VO$_2$max.

In an eighth aspect the present invention provides a method for metabolomically evaluating a subject's biological age. The method can include the steps of obtaining a sample from the subject, generating a small molecule profile of metabolites from the subject using samples collected from the subject, and comparing the levels of a plurality of small molecules of the subject in the generated small molecule profile to known standards established for a population of subjects of the same or similar chronological age using a plurality of small molecule metabolomic markers indicative of the biological age of the population of subjects.

In an ninth aspect the present invention provides a method of screening for the presence, absence or level(s) of one or more metabolites in a subject. The method can include the steps of obtaining a blood or plasma sample from the subject, extracting small molecule metabolites from the blood or plasma sample, performing liquid chromatography-mass spectrometry on the extracted sample to screen for the presence, absence or level(s) of one or metabolites comprising 6-Lactoyl-5-6-7-8-tetrahydropterin, Phaseolic acid, Anandamide, L-Homocitrulline, 4-Nitroaniline, Felbamate, 10-Hydroxydecanoic acid, Inositol 1-2-3-5-6-pentakisphosphate, Citrate, acyl-C18:2-OH, Phosphoserine, 1stgna-4-9 (11)-diene-3-20-dione, Indole-3-acetate, 4-Hydroxybenzoate, Tetradecenoyl Carnitine, O-Dodecenoyl-carnitine, O-Decenoyl-L-carnitine, Putrescine, 6-Thioxanthine 5-monophosphate, Theogallin, and Pantetheine.

In a tenth aspect the present invention provides a second method of screening for the presence, absence or level(s) of one or more metabolites in a subject. The method can include the steps of obtaining a sample from the subject, generating a small molecule profile of metabolites from the subject using samples collected from the subject to screen for the presence, absence or level(s) of one or metabolites comprising 6-Lactoyl-5-6-7-8-tetrahydropterin, Phaseolic acid, Anandamide, L-Homocitrulline, 4-Nitroaniline, Felbamate, 10-Hydroxydecanoic acid, Inositol 1-2-3-5-6-pentakisphosphate, Citrate, acyl-C18:2-OH, Phosphoserine, 1stgna-4-9(11)-diene-3-20-dione, Indole-3-acetate, 4-Hydroxybenzoate, Tetradecenoyl Carnitine, O-Dodecenoyl-carnitine, O-Decenoyl-L-carnitine, Putrescine, 6-Thioxanthine 5-monophosphate, Theogallin, Pantetheine, Oxaloacetate, Acyl-C5-OH, 2-Phospho-D-Glycerate, Ascorbate, Selenohomocystine, 5-Acetylamino-6-formylamino-3-methyluracil, Phosphate, and Octylamine.

BRIEF DESCRIPTION OF THE DRAWINGS

For a fuller understanding of the invention, reference should be made to the following detailed description, taken in connection with the accompanying drawings, in which:

FIG. 3C is an enlarged presentation of FIG. 3B.

DETAILED DESCRIPTION OF THE PREFERRED EMBODIMENT

Figure 1:
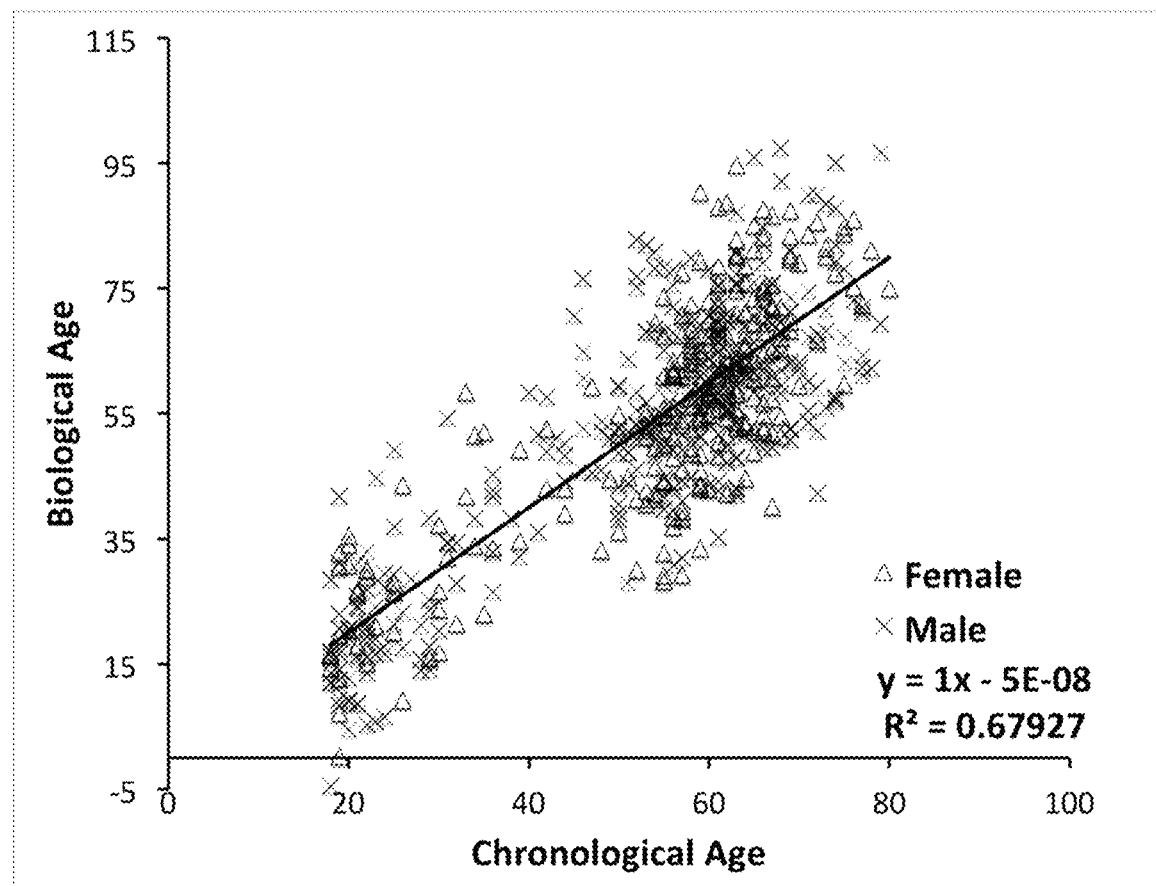
FIG. 1 is a graph showing that biological age and chronological age are significantly correlated in the training cohort of 604 healthy adults ($R^2=0.68$, P-value <0.0001).

Chronological age is an important predictor of morbidity and mortality, however it is unable to account for heterogeneity in the decline of physiological function and health with advancing age. Several attempts have been made to instead define a "biological age" using multiple physiological parameters in order to account for variation in the trajectory of human aging; however, these methods require technical expertise and are likely too time-intensive and costly to be implemented into clinical practice. Accordingly, a metabolomic signature of biological aging was developed that can predict changes in physiological function with the convenience of a blood sample. A weighted model of biological age was generated based on multiple clinical and physiological measures in a large group of healthy adults and was then applied to a cohort of healthy older adults who were tracked longitudinally over a 5-10 year timeframe. Plasma metabolomic signatures were identified that were associated with biological age, including some that could predict whether individuals would age at a faster or slower rate. These results not only have clinical implications by providing a simple blood-based assay of biological aging, but also provide insight into the molecular mechanisms underlying human healthspan.

The metabolome, defined as all small molecules characterizing a biological system, is altered with age and reflective of age-related changes in physiological function. The metabolome therefore provides the unique opportunity to investigate systemic molecular changes in vivo. Metabolomics were utilized to identify the molecular events associated with biological aging in healthy adults. After generating a model of biological age from clinical and physiological measures in a large cohort of healthy adults, an algorithm was applied to a longitudinal cohort representative of healthy aging. Using metabolomics analysis of plasma collected at baseline and follow-up, small molecule signatures were identified that are associated with biological aging in middle-aged and older adults, including metabolites that are predictive of faster vs. slower aging.

Despite a growing body of literature, there is little consensus regarding the most appropriate method for determining biological age in humans. One popular approach has been to measure the levels of circulating biomarkers that are strongly correlated with chronological age such as the calculation of DNA methylation (DNAm) age using age-related CpG methylation sites within circulating leukocytes (Hannum et al. 2013; Horvath 2013). While this approach is convenient, the ability of DNAm age to predict mortality is lost after adjusting for chronological age (Kim et al., 2017), suggesting that these circulating biomarkers may be more related to the passage of time than a true indicator of human healthspan. An alternative approach is to define biological age using clinical and physiological parameters that are closely associated with age-related disease risk. Such models predict mortality better than those based only on chronological age-related molecular markers (Levine 2013; Belsky et al. 2015; Kim et al. 2017), but are more costly, time-consuming and require specialized training and equipment to measure, thus limiting their practicality in primary care or other clinical settings.

A hybrid approach was adopted in which a model of biological aging was first developed using clinical and physiological parameters indicative of risk for age-related disease and disability. In the next stage, sets of circulating metabolites were identified that are associated with, and/or predictive of biological age, thereby merging clinically relevant parameters with the simplicity of a blood sample. In general, several metabolites were identified that are associated with both baseline biological age and the future rate of aging that are known to be involved in the regulation of energy homeostasis (e.g., fatty acid metabolism). Cellular energy metabolism is tightly controlled and its dysregulation has been implicated as a central mechanism, or "hallmark", of age-associated physiological declines (Finkel 2015; López-Otín et al. 2016); thus, this study offers new indicators of aging trajectories that can indicate which individuals might be best targeted for early intervention.

Age-related changes to energy homeostasis pathways are tightly linked with changes in mitochondrial function, and both have been implicated as central mechanisms in the development age-related physiological dysfunction (Kujoth et al. 2005; Houtkooper et al. 2010; Hardie et al. 2012; Lopez-Otin et al. 2013; Verdin 2015; Wang & Hekimi 2015; Wiley et al. 2016). In the model taught herein, higher levels of carnitines (tetradecenoyl carnitine, O-dodecenoyl-carnitine, O-decenoyl-L-carnitine), necessary for fatty acid metabolism, were associated with lower biological ages at baseline. Elevated levels of carnitine metabolites may be indicative of increased capacity for fatty acid utilization, as reduced carnitine levels with age have been demonstrated to reduce mitochondrial performance (Noland et al. 2009). Additionally, lower biological age was also associated with higher levels of the TCA cycle intermediate citrate, indicating a greater capacity of the TCA cycle to produce ATP. Together, these findings indicate that lower biological age is associated with the potential for greater metabolic flux.

Metabolites associated with energy metabolism were also related to an individual's future rate of biological aging. Elevated 2-phospho-D-glycerate (glycolysis) was associated with a slower rate of future aging, higher concentrations of acyl-C5-OH (carnitine and fatty acid metabolism) and oxaloacetate (TCA cycle) were associated with a faster rate of biological aging in the future. These relations are in contrast to our other findings, which demonstrated that metabolites involved in carnitine and fatty acid metabolism were associated with younger biological age at baseline. Although these results are paradoxical in nature, they consistently implicate energy metabolism and highlight these pathways for future study. The analysis detailed herein also highlighted amino acid metabolism in addition to energy homeostasis pathways. Circulating levels of L-methionine were positively associated with a faster rate of biological aging, which is in line with previous findings that L-methionine restriction is associated with preserved physiological function in preclinical models during aging (Sun et al. 2009; Hasek et al. 2010). These relations support the association between biological aging and mitochondrial dysfunction (Koves et al. 2008), and converge upon basic energy sensing mechanisms conserved across numerous organisms.

This analysis demonstrates that circulating plasma metabolomic profiles are associated with the rate at which changes in biological age occur, which is important in determining the molecular underpinnings of aging. The novel set of blood-based markers of biological aging have potential applications in both biomedical research and clinical practice. In research settings, this approach provides an avenue to more efficiently test and validate novel interventions designed to target the basic mechanisms of human aging. Such trials will take years before their success can be confirmed; however, blood-based markers of biological age could be measured more frequently at intermediate time points and provide earlier insight into the potential of an intervention for slowing the aging.

The unique blood-based markers of biological age taught herein could also be used in the primary care setting to more efficiently and cost-effectively track disease risk over time, and possibly screen candidates for more labor-intensive follow-up testing. For example, low cardiorespiratory fitness (usually assessed by measuring $VO_2$ max) is a known risk factor for cardiovascular and all-cause mortality in older adults (Blair et al. 1989; Laukkanen et al. 2004; Sui et al. 2007); however, it is not regularly assessed in the primary care setting due to costs and logistical challenges (Ross et al. 2016). Although non-exercise, regression-based prediction models of cardiorespiratory fitness currently exist (Jackson et al. 1990; Bradshaw et al. 2005; Cao et al. 2010; Nes et al. 2011), these models are typically based off of basic characteristics such as age, sex and body composition (Ross et al. 2016) and may not capture more subtle differences among healthy, asymptomatic older adults. Because the plasma metabolome is thought to more closely reflect changes in physiological function (Soltow et al. 2010; Barallobre-Barreiro et al. 2013), these unique signatures of biological aging may be more capable of identifying subclinical changes indicative of worsening function, such as low cardiorespiratory fitness, thereby triggering earlier follow-up testing and implementation of preventive measures such as lifestyle modifications or pharmaceutical therapeutics.

The present invention provides unique metabolomic signatures that are associated with the rate of human biological aging, and will prove useful for the rapid detection of older adults at risk for physiological dysfunction. The present model of biological aging and subsequent molecular analyses have established an approach to investigate the molecular foundation of biological aging in humans.

Example 1—Selection of Healthspan Indicators and Calculation of Biological Age

Figure 5:
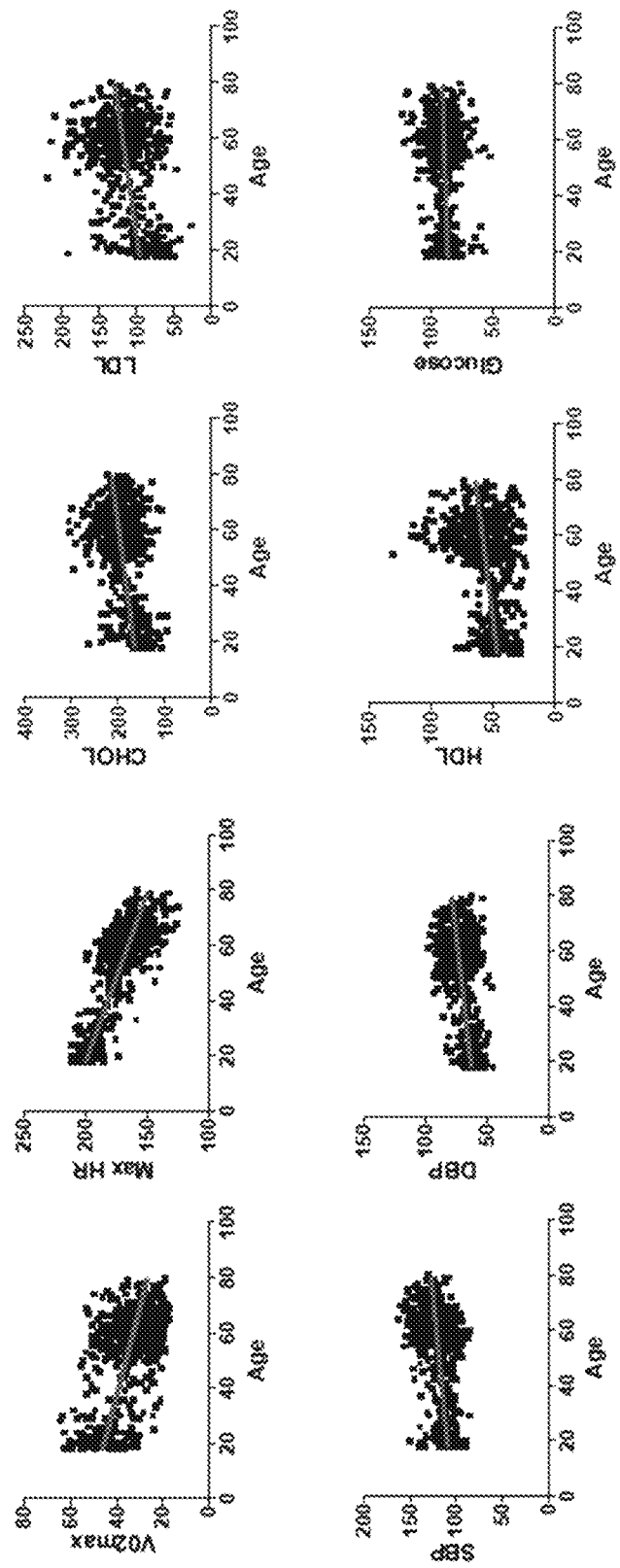
FIG. 5 is a set of thirteen (13) graphs showing regressions demonstrating the relation of clinical and physiological markers with age.

Thirteen (13) clinical and physiological indicators of human healthspan were used to generate a model biological age (Table 1) (Klemera & Doubal 2006; Belsky et al. 2015). Briefly, select clinical and physiological measures were evaluated for their relation to chronological age using individual linear regressions and necessary components of these regressions were incorporated into a weighted equation to calculate biological age. The slope, intercept, and standard deviation of the residuals for each measure's relation to chronological age were incorporated into the equation (see "Methods" as described in Example 4, below, for complete description). The selection of healthspan indicators was based on their association with chronological age in an independent training cohort (FIG. 5) and/or their relevance to age-related disease risk (Calle et al. 1999). The training cohort consisted of 604 healthy adults (aged 18-80 years), who had previously undergone testing in our laboratory between 2003 and 2017. Importantly, all subjects were free of clinical disease and disability at the time of testing as confirmed by a medical history and physical examination and all healthspan indicators were within normal healthy ranges, providing a unique opportunity to address the effects of primary aging (Table 1). Due to inherent sex-related differences of several biomarkers included in the model, such as body composition and maximal aerobic capacity (Fleg et al. 2005; Wells 2007), separate models of biological age were created from our training cohort allowing us to compare men and women on the same scale for all subsequent analyses.

Figure 2:
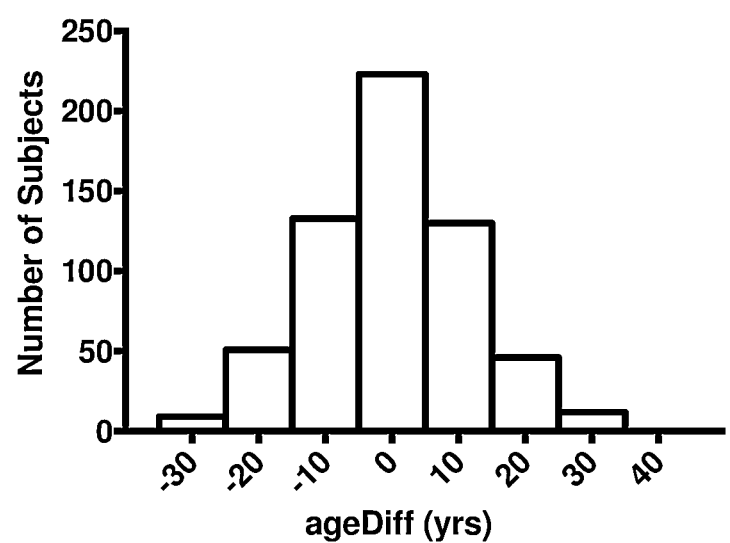
FIG. 2 is a graph showing that ageDiff was calculated, and although most individual's biological age is within 5 years of their chronological age, many demonstrate greater differences between biological age and chronological age.

Biological age was significantly correlated with chronological age (FIG. 1, $R^2$=0.68, P<0.0001; both sexes combined); however, variability among subjects of similar age was observed and reflects the expected heterogeneity of biological aging. To explore this heterogeneity further, we calculated each individual's 'ageDiff'—the mathematical difference (in years) between biological age and chronological age (Kim et al. 2017). A positive ageDiff implies that an individual is biologically older than their chronological age would suggest. In this regard, we observed a normal distribution of ageDiff across our training cohort (FIG. 2), suggesting that our model is sensitive to detect a wide range of differences in biological age.

TABLE 1

Training cohort subject characteristics.

| Subject Characteristics | Male | Female |
|---|---|---|
| Subjects (n) | 355 | 249 |
| Avg. Age (range) | 52 (18-79) | 55 (18-80) |

TABLE 1-continued

Training cohort subject characteristics.

| Subject Characteristics | Male | Female |
|---|---|---|
| Body Mass Index (kg/m2) | 26 ± 0.21 | 24 ± 0.25 |
| Waist-to-Hip Ratio | 0.89 ± 0.003 | 0.76 ± 0.004 |
| Body Fat (%) | 24 ± 1 | 34 ± 1 |
| Bone Mineral Density (g/cm2) | 1.27 ± 0.01 | 1.14 ± 0.01 |
| Systolic Blood Pressure (mmHg) | 122 ± 1 | 116 ± 1 |
| Diastolic Blood Pressure (mmHg) | 74 ± 1 | 69 ± 1 |
| Glucose (mg/dL) | 90 ± 1 | 87 ± 1 |
| Total Cholesterol (mg/dL) | 189 ± 2 | 200 ± 2 |
| LDL-C (mg/dL) | 116 ± 2 | 116 ± 2 |
| HDL-C (mg/dL) | 50 ± 1 | 66 ± 1 |
| eGFR (mL/min/1.73 m2) | 78 ± 1 | 75 ± 1 |
| Max Heart Rate (bpm) | 173 ± 1 | 168 ± 1 |
| VO2max (mL/kg/min) | 37.9 ± 0.5 | 30.7 ± 0.5 |

Data are mean ± SEM; LDL-C, low-density lipoprotein cholesterol; VLDL-C, very low density lipoprotein cholesterol; HDL-C, high-density lipoprotein cholesterol; eGFR, estimated glomerular filtration rate; VO2max, maximal oxygen consumption.

Example 2—Rate of Biological Aging in an Independent Longitudinal Cohort

Using the sex-specific regression coefficients derived from the training models, a biological age was calculated in a separate set of 31 healthy middle-aged and older adult men and postmenopausal women at two separate time points (Table 2). Subjects included individuals who had undergone testing in our laboratory between 5-10 years prior and agreed to return to the laboratory for follow-up assessments. All subjects were free of chronic disease or disability at the time of initial enrollment and remained mostly healthy over the time to follow-up, which averaged 8.6 years. Only late middle-aged and older adults were included in this longitudinal cohort to maximize the ability to detect changes in biological age within the relatively short follow-up period.

Figure 3:
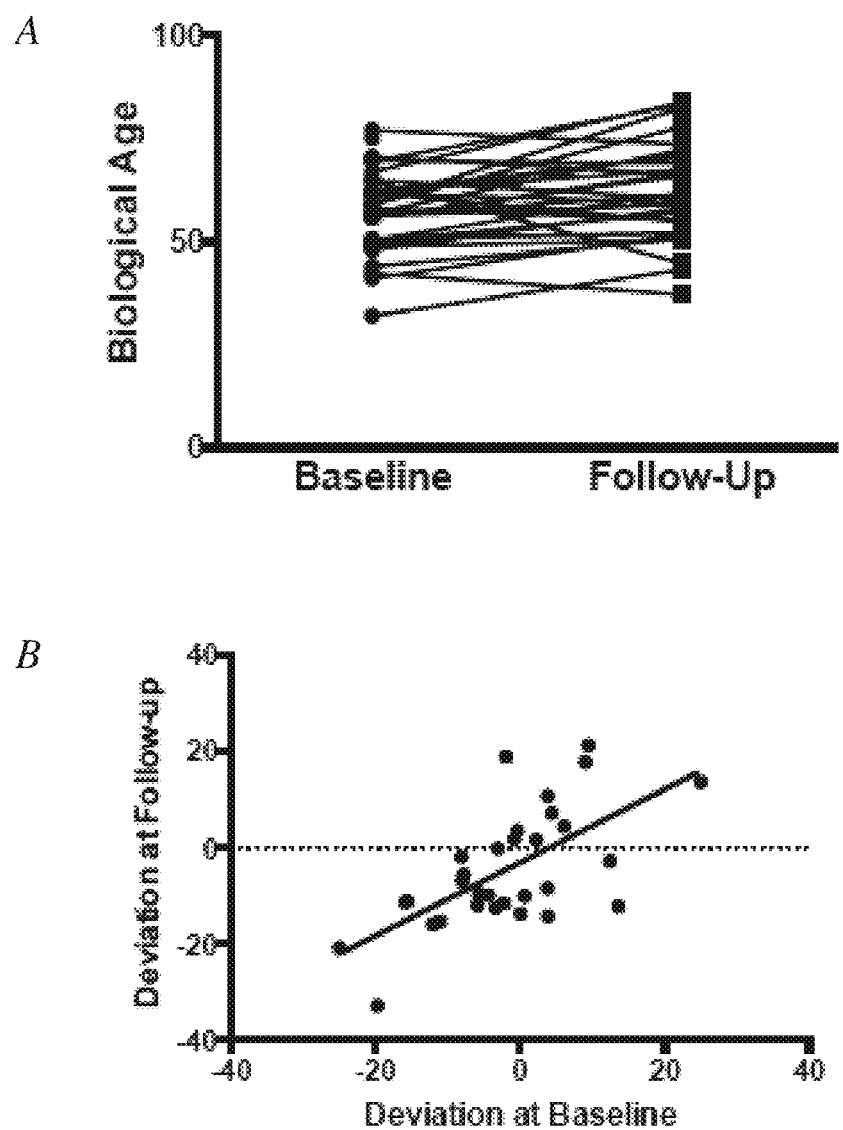
FIG. 3 is a pair of graphs addressing longitudinal studies. (A) Change in biological age, calculated from clinical and physiological measures, in our longitudinal cohort. Although the change in biological age is significant (P<0.01), the trajectories of aging are highly variable. (B) Significant relation between ageDiff at baseline and follow-up (P<0.001).

Overall, a significant increase in mean biological age was observed in the longitudinal cohort from baseline to follow-up of approximately six biological aging years suggesting that, as a group, the longitudinal cohort aged slower than expected over the time to follow-up (FIG. 3A). This may have been due in part to a slight decrease in LDL and total cholesterol (Table 2), which was most likely due to initiation of cholesterol-lowering medications in several of the subjects. Interestingly, ageDiff at baseline was significantly associated with ageDiff at follow-up, suggesting that individuals who were biologically older than their chronological age at baseline were likely to remain relatively older than their chronological age at follow-up, and vice-versa (FIG. 3B).

Figure 4:
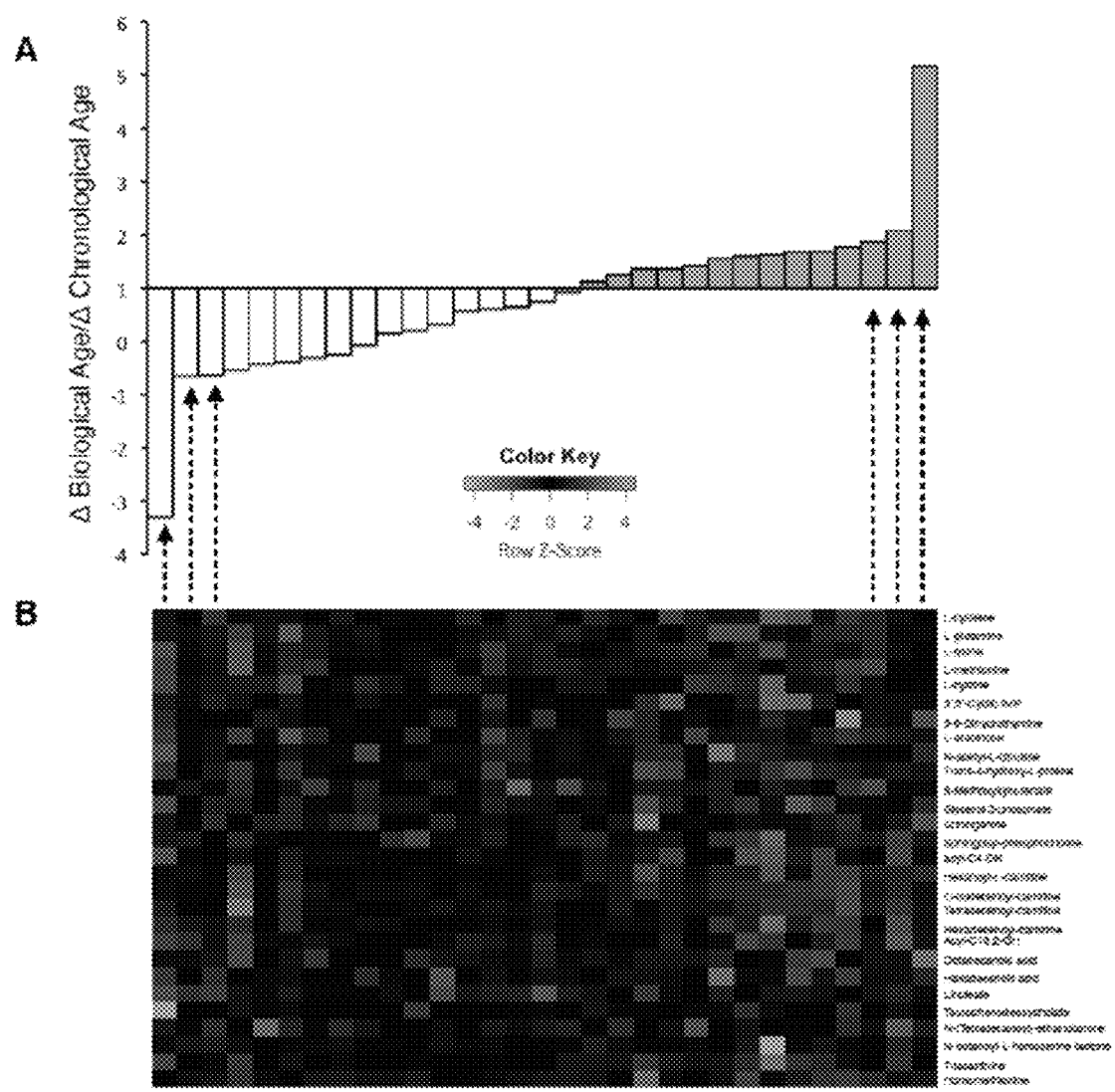
FIG. 4 is a graph and a pair of heatmaps. (A) Rate of biological aging for each individual in the longitudinal cohort. A ratio smaller than one indicates slower aging, while a ratio greater than one indicates faster aging. (B) Heatmap of the change in abundance of 28 metabolites significantly associated with rate of biological aging. Individuals are aligned in columns, metabolites in rows. (C)

Finally, to determine the rate of biological aging over the follow-up period, changes in biological age to changes in chronological age were normalized. This resulted in a ratio in which a value above or below one (1) is indicative of faster vs. slower biological aging, respectively. A continuous distribution in the rate of biological aging across our longitudinal cohort was observed, with approximately half of all subjects exhibiting faster biological aging and the other half exhibiting slower biological aging (FIG. 4A).

TABLE 2

Subject characteristics of our longitudinal cohort.

| Subject Characteristics | Baseline | Follow-Up |
|---|---|---|
| Sex (M/F) | 20/11 | |
| Age (yrs) | 59 ± 1 | 68 ± 1* |
| Body Mass Index (kg/m2) | 25 ± 1 | 25 ± 1 |
| Waist-to-Hip Ratio | 0.86 ± 0.02 | 0.86 ± 0.02 |

TABLE 2-continued

Subject characteristics of our longitudinal cohort.

| Subject Characteristics | Baseline | Follow-Up |
|---|---|---|
| Body Fat (%) | 26 ± 2 | 27 ± 2 |
| Bone Mineral Density (g/cm2) | 1.23 ± 0.02 | 1.21 ± 0.02* |
| Systolic Blood Pressure (mmHg) | 119 ± 2 | 123 ± 2 |
| Diastolic Blood Pressure (mmHg) | 73 ± 2 | 73 ± 1 |
| Glucose (mg/dL) | 89 ± 2 | 85 ± 1* |
| Total Cholesterol (mg/dL) | 204 ± 5 | 172 ± 5* |
| LDL-C (mg/dL) | 124 ± 4 | 100 ± 4* |
| HDL-C (mg/dL) | 57 ± 3 | 54 ± 3* |
| eGFR (mL/min/1.73 m2) | 71 ± 2 | 78 ± 3 |
| Max Heart Rate (bpm) | 168 ± 2 | 156 ± 3* |
| VO2max (mL/kg/min) | 36.1 ± 1.7 | 31.5 ± 1.5* |

Data are mean ± SEM; LDL-C, low-density lipoprotein cholesterol; VLDL-C, very low density lipoprotein cholesterol; HDL-C, high-density lipoprotein cholesterol; eGFR, estimated glomerular filtration rate; VO2max, maximal oxygen consumption.
*P < 0.05 vs baseline.

Example 3—The Plasma Metabolome as a Predictor of Biological Aging

Because the determination of biological age based off of clinical and physiological indicators is time-consuming and technically challenging, circulating metabolites were identified that can serve as novel biomarkers of biological aging. To do this we measured the abundance of 360 individual metabolites in the plasma of the longitudinal subjects at both time points using liquid chromatography and mass spectroscopy (LC-MS). To account for any transient changes in the metabolome within an individual due to modifications to dietary consumption, macronutrient compositions were included as covariates in the baseline statistical models. Because the percent of each macro-nutrient in the diet showed no differences from baseline to follow-up, suggesting stability in diet over time, dietary intakes were not included in the longitudinal analyses.

Figure 6:
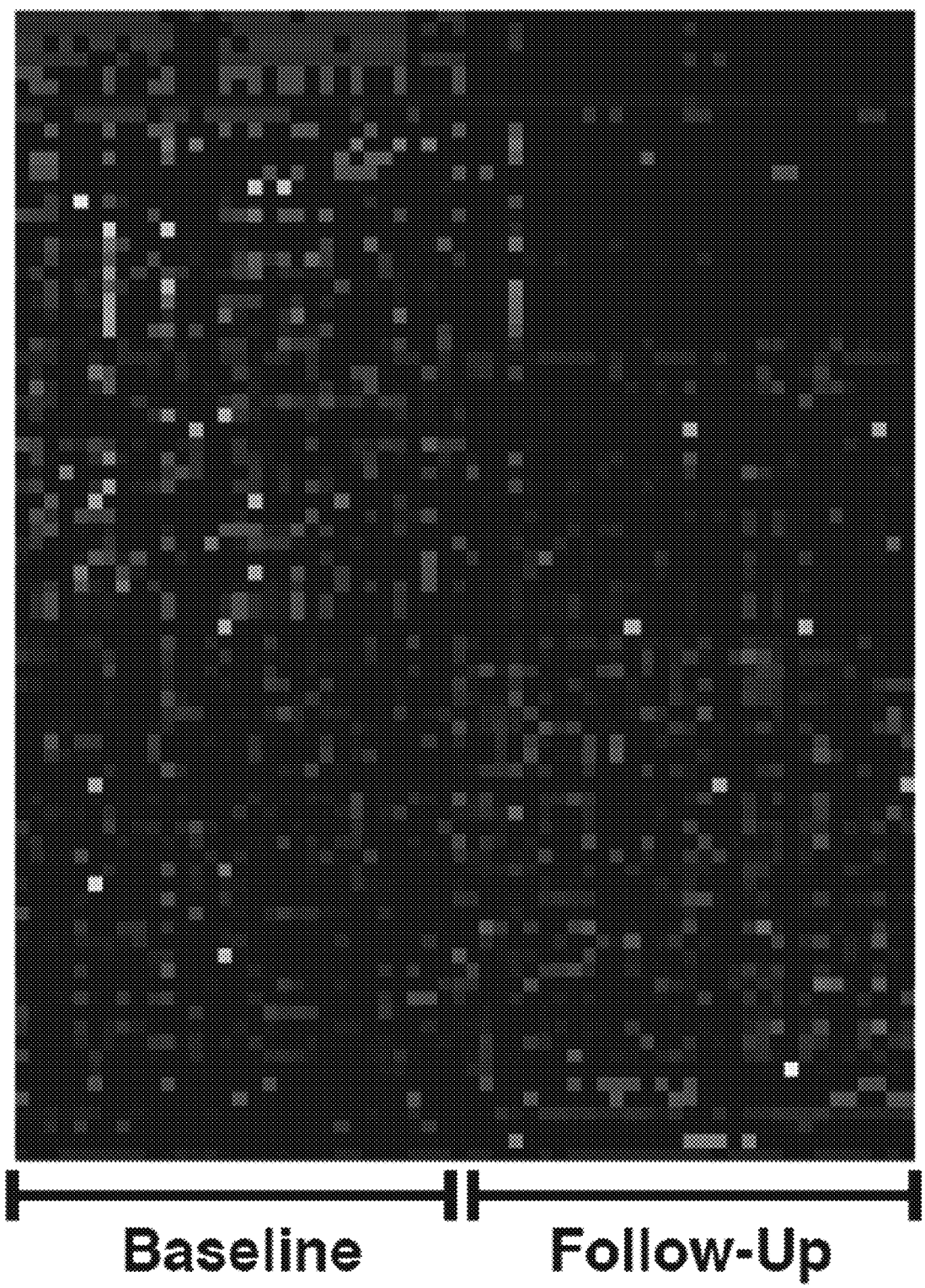
FIG. 6 is a heatmap showing that 81 metabolites (of 360 measured) measured in plasma of individuals from the longitudinal cohort were significantly different between baseline and follow-up at P<0.05, 0.1.

In total, eighty-one (81) metabolites were significantly altered from baseline to follow-up in the longitudinal cohort, confirming that age-related changes are detectable in the plasma metabolome over a relatively short period of time (FIG. 6 and Table 6). To determine if any of these changes were also indicative of biological aging, changes in the metabolome (normalized to follow-up time) were compared to the rate biological aging and 28 metabolites were identified that were significantly associated with the rate of biological aging (FIG. 4B—see also Table 5). Interestingly, more robust changes in metabolite abundance in either direction, as indicated by a higher or lower Z-score, appeared to occur in those individuals who exhibited the fastest or slowest biological aging, respectively (FIG. 4A). The metabolites most associated with the rate of biological aging included amino acid, fatty acid, acylcarnitine, sphingolipid, and nucleotide metabolites.

Although determining an individual's actual rate of biological aging holds clinical value (e.g., precision medicine), it is technically challenging and requires repeat assessments of multiple clinical and physiological parameters, making it difficult to implement into clinical practice. Therefore, the ultimate goal was to a) identify baseline metabolomic signatures indicative of one's biological age at a single time-point and b) predict one's future rate of biological aging (i.e., if someone is at risk for faster vs. slower aging).

Metabolites Associated with Biological Age:

To understand if the plasma metabolome is reflective of one's biological age, we explored whether metabolite abundances measured at baseline are associated with an individual's biological age at the same timepoint, while controlling for chronological age and dietary macronutrient content in the analysis. Three individuals did not complete all necessary dietary records and were therefore excluded from this regression analysis due to missing values, although the elimination of these subjects did not change group characteristics (Table 4). In total, 21 metabolites were related to biological age, 16 of which were endogenous or secondary metabolites of microbe metabolism (Table 3). Greater abundances of metabolites associated with folate (6-lactoyl-5-6-7-8 tetrahydropterin), fatty acyl (phaseolic acid), ethanolamine (anandamide), and carboxylic acid (L-homocitrulline) metabolism were observed in individuals who were biologically older. Alternatively, greater concentrations of metabolites from carnitine and fatty acid metabolism (10-hydroxydecanoic acid, O-dodecanoyl-carnitine, tetradecenoyl carnitine, O-decenoyl-L-carnitine, acyl-C18:2-OH), TCA cycle (citrate), polyamine (putrescine), inositol (inositol 1-2-3-5-6-pentakisphosphate), sterol (pregna-4,9(11)-diene-3,20-dione), serine (phosphoserine), indole (indole-3-acetate), and ubiquinone (4-hydroxybenzoate) pathways were associated with a lower biological age.

TABLE 3

Association of metabolite concentrations with biological age at baseline.
Non-endogenous metabolites notated in italic text.

| Metabolite | Estimate | Error | P-Value |
|---|---|---|---|
| Greater Values Indicative of Higher Biological Age | | | |
| 6-Lactoyl-5-6-7-8-tetrahydropterin | 9.45E-06 | 4.07E-06 | 0.03 |
| Phaseolic acid | 1.23E-05 | 5.23E-06 | 0.03 |
| Anandamide | 4.56E-04 | 1.82E-04 | 0.02 |
| L-Homocitrulline | 2.61E-03 | 1.07E-03 | 0.02 |
| 4-Nitroaniline | 2.63E-06 | 8.61E-07 | 0.006 |
| Felbamate | 4.40E-06 | 1.82E-06 | 0.02 |
| Greater Values Indicative of Lower Biological Age | | | |
| 10-Hydroxydecanoic acid | -1.17E-04 | 4.35E-05 | 0.01 |
| Inositol 1-2-3-5-6-pentakisphosphate | -3.95E-04 | 1.52E-04 | 0.02 |
| Citrate | -1.27E-06 | 5.15E-07 | 0.02 |
| acyl-C18:2-OH | -3.00E-04 | 1.22E-04 | 0.02 |
| Phosphoserine | -1.57E-05 | 6.56E-06 | 0.03 |
| 1stgna-4-9(11)-diene-3-20-dione | -1.54E-04 | 6.56E-05 | 0.03 |
| Indole-3-acetate | -6.64E-06 | 2.87E-06 | 0.03 |
| 4-Hydroxybenzoate | -1.26E-07 | 5.56E-08 | 0.03 |
| Tetradecenoyl Carnitine | -5.57E-06 | 2.47E-06 | 0.03 |
| O-Dodecenoyl-carnitine | -5.90E-06 | 2.69E-06 | 0.04 |
| O-Decenoyl-L-carnitine | -3.40E-06 | 1.60E-06 | 0.045 |
| Putrescine | -7.86E-04 | 3.76E-04 | 0.048 |
| 6-Thioxanthine 5-monophosphate | 5.87E-05 | 1.88E-05 | 0.004 |
| Theogallin | 5.53E-06 | 1.67E-07 | 0.003 |
| Pantetheine | 5.80E-06 | 2.21E-06 | 0.02 |

TABLE 4

Subject Characteristics of entire longitudinal cohort (31 subjects) compared with individuals with full dietary data and included in baseline metabolomics analyses of biological age (28 subjects). Data are mean ± SEM; LDL-C, low-density lipoprotein cholesterol; VLDL-C, very low-density lipoprotein cholesterol; HDL-C, high-density lipoprotein cholesterol; eGFR, estimated glomerular filtration rate; VO$_2$max, maximal oxygen consumption.
No significant differences were observed.

| Subject Characteristics | All Subjects | Dietary Analysis Subjects |
|---|---|---|
| Sex (M/F) | 20/11 | 17/11 |
| Age (yrs) | 59 ± 1 | 60 ± 1 |
| Body Mass Index (kg/m$^2$) | 25 ± 1 | 25 ± 1 |
| Waist-to-Hip Ratio | 0.86 ± 0.02 | 0.85 ± 0.02 |
| Body Fat (%) | 26 ± 2 | 26 ± 2 |
| Bone Mineral Density (g/cm$^2$) | 1.23 ± 0.02 | 1.23 ± 0.02 |
| Systolic Blood Pressure (mmHg) | 119 ± 2 | 118 ± 2 |
| Diastolic Blood Pressure (mmHg) | 73 ± 2 | 73 ± 2 |
| Glucose (mg/dL) | 89 ± 2 | 89 ± 2 |
| Total Cholesterol (mg/dL) | 204 ± 5 | 201 ± 5 |
| LDL-C (mg/dL) | 124 ± 4 | 123 ± 4 |
| HDL-C (mg/dL) | 57 ± 3 | 57 ± 3 |
| eGFR (mL/min/1.73 m$^2$) | 71 ± 2 | 70 ± 3 |
| Max Heart Rate (bpm) | 168 ± 2 | 167 ± 2 |
| VO$_2$max (mL/kg/min) | 36.1 ± 1.7 | 36.4 ± 1.8 |

Predicting Faster Vs. Slower Aging:

Finally, after determining that the plasma metabolome is associated with biological age, we sought to determine if the concentrations of specific metabolites among individuals at baseline could predict whether an individual would experience faster or slower biological aging over the time to follow-up. Eight (8) metabolites measured at baseline predicted the rate of biological aging in our longitudinal cohort (Table 5). Of these, two metabolites were associated with fatty acid/TCA cycle metabolism (acyl-C5-OH and oxaloacetate) and were positively associated with faster aging, whereas six metabolites related to glycolysis (2-phospho-D-glycerate), nucleotide (phosphate), glutathione (ascorbate), caffeine metabolism (5-acetylamino-6-formylamino-3-methyluracil), amino acid metabolism (selenohomocystine) and one exogenous metabolite (octylamine) were positively associated with a slower aging phenotype.

TABLE 5

Metabolite concentrations at baseline are significantly associated with future faster or slower rate of aging.
Non-endogenous metabolites notated in italic text.

| Metabolite | Estimate | Error | P-Value |
|---|---|---|---|
| Greater Values Indicative of Future Faster Aging | | | |
| Oxaloacetate | 7.79E-06 | 3.15E-06 | 0.02 |
| Acyl-C5-OH | 9.02E-06 | 3.42E-06 | 0.02 |
| Greater Values Indicative of Future Slower Aging | | | |
| 2-Phospho-D-Glycerate | -1.98E-05 | 7.49E-06 | 0.01 |
| Ascorbate | -2.45E-06 | 9.89E-06 | 0.02 |
| Selenohomocystine | -8.37E-07 | 3.70E-07 | 0.03 |
| 5-Acetylamino-6-formylamino-3-methyluracil | -4.27E-07 | 1.96E-07 | 0.04 |
| Phosphate | -9.63E-08 | 4.45E-08 | 0.04 |
| Octylamine | -2.65E-07 | 1.24E-07 | 0.04 |

Example 4—Materials and Methods

Study Design and Subjects

All study procedures were reviewed and approved by the University of Colorado Boulder Institutional Review Board. Clinical and physiological measurements were performed at the University of Colorado Boulder Clinical Translational Research Center (CTRC). All study participants provided written informed consent after the nature, benefits and risks of the study were explained. Subjects from the longitudinal cohort were re-contacted after at least five years and provided an option to re-enroll. All subjects were non-smokers, determined to be free of clinical disease as assessed by medical history, physical examination, blood chemistries, and resting and exercise ECG. To control for their menstrual cycle, premenopausal women were studied during the early follicular phase, while older women were postmenopausal for at least one year. All subjects followed a 12-hour fast and 24 hour abstention from alcohol, exercise, and prescription medication prior to testing.

Model of Biological Age

Biological age was calculated using the basic Klemera-Doubal equation without chronological age as a marker (Klemera & Doubal 2006). Parameters for the 13 clinical and physiological measures used in the model were estimated from cross-sectional data in 355 men and 249 women (Table 1), generating separate equations for biological age in males and females due to basic differences in physiology. Specifically, a linear relationship with chronological age was estimated in men and women for each measure by individual linear regressions. Biological age ($BA_E$) for an individual with measurements ($x_j$) was calculated by the Klemera-Doubal equation with m=13:

$$BA_E = \frac{\sum_{j=1}^{m}(x_j - q_j)\frac{k_j}{s_j^2}}{\sum_{j=1}^{m}\left(\frac{k_j}{s_j}\right)^2},$$

Where $k_j$ is the slope, $q_j$ the intercept, and $s_j$ the standard deviation of residuals for the corresponding regression. Once the model was trained on our initial cohort of 604 individuals, the equation was applied to a longitudinal cohort of 31 individuals to determine rates of aging, calculated as the ratio of (Δ biological age:Δ chronological age). ageDiff was calculated by assessing the difference in calculated biological age from chronological age at baseline.

Dietary Analysis

Each participant was instructed to complete a three-day food record (two weekdays and one weekend day) at each time point. Participants were provided with verbal and written instructions for reporting food intake including providing accurate descriptions of the foods consumed as well as estimated portion sizes. Upon completion, food records were checked for accuracy. Food Processor SQL Nutrition and Fitness Program (ESHA Research, Salem, OR, USA) was used for analysis. Percent calories from fat, protein, and carbohydrates were calculated for each individual, and differences in the distribution of these dietary variables were assessed using paired t-tests and deemed significant at P<0.05.

Metabolomics Analysis

Sample Preparation: Plasma was isolated from subjects and stored at −80° C. until analysis. Prior to LC-MS analysis, samples were diluted 1:10 (v/v) with methanol:acetonitrile:water (5:3:2, v:v). Suspensions were vortexed continuously for 30 min at 4° C. Insoluble material was removed by centrifugation at 10,000 g for 10 min at 4° C. and supernatants were isolated for metabolomics analysis by UHPLC-MS.

UHPLC-MS analysis: Analyses were performed as previously published (Nemkov et al. 2017). Briefly, the analytical platform employs a Vanquish UHPLC system (Thermo Fisher Scientific, San Jose, CA, USA) coupled online to a Q Exactive mass spectrometer (Thermo Fisher Scientific, San Jose, CA, USA). Plasma extracts (10 µl) were resolved over a Kinetex C18 column, 2.1×150 mm, 1.7 µm particle size (Phenomenex, Torrance, CA, USA) equipped with a guard column (SecurityGuard™ Ultracartridge— UHPLC C18 for 2.1 mm ID Columns—AJO-8782—Phenomenex, Torrance, CA, USA) using an aqueous phase (A) of water and 0.1% formic acid and a mobile phase (B) of acetonitrile and 0.1% formic acid. Samples were eluted from the column using either an isocratic elution of 5% B flowed at 250 µl/min and 25° C. or a gradient from 5% to 95% B over 1 minute, followed by an isocratic hold at 95% B for 2 minutes, flowed at 400 µl/min and 30° C. The Q Exactive mass spectrometer (Thermo Fisher Scientific, San Jose, CA, USA) was operated independently in positive or negative ion mode, scanning in Full MS mode (2 µscans) from 60 to 900 m/z at 70,000 resolution, with 4 kV spray voltage, 15 shealth gas, 5 auxiliary gas. Calibration was performed prior to analysis using the Pierce™ Positive and Negative Ion Calibration Solutions (Thermo Fisher Scientific). Acquired data was then converted from .raw to .mzXML file format using Mass Matrix (Cleveland, OH, USA). Samples were analyzed in randomized order with a technical mixture injected after every 15 samples to qualify instrument performance. Metabolite assignments, isotopologue distributions, and correction for expected natural abundances of deuterium, $^{13}C$, and $^{15}N$ isotopes were performed using MAVEN (Princeton, NJ, USA) (Clasquin et al. 2012). Metabolic pathway analysis was performed using the Metabo Analyst 3.0 package (www.metaboanalyst.com) (Xia & Wishart 2016).

Statistics: The relation between chronological age and biological age in our initial training cohort was established using Pearson Correlation analysis. Additional comparisons between measures made at baseline and follow-up in the longitudinal cohort were performed using paired t-tests and deemed significant at P<0.05. For metabolomics analysis, features between the two time-points in the longitudinal cohort with p-value <0.05 resulting from a two-tailed t-test and a false-discovery rate (FDR)<0.1 were classified as significant. To identify metabolites related with rate of aging, differences in metabolite concentrations were calculated and associated with rate of biological aging. Subsequent independent linear regressions were employed to understand the relation between metabolite abundances, future rate of aging, and biological age while using percent calories from total fat, protein, and carbohydrate as covariates. Because three individuals did not complete all necessary dietary records, they were excluded and 28 individuals were included in the regression analyses. Removal of 3 individuals with missing dietary values did not change overall subject characteristics (Table 4).

TABLE 6

Metabolites that were significantly altered from baseline to follow-up.

| Compounds | t.stat | p.value | −LOG10(p) | FDR |
|---|---|---|---|---|
| Phaseolic acid | −13.034 | 7.75E−19 | 18.111 | 1.43E−16 |
| Felbamate | −12.833 | 7.99E−19 | 18.098 | 1.43E−16 |
| 6-Lactoyl-5-6-7-8-tetrahydropterin | −10.802 | 8.98E−16 | 15.047 | 1.07E−13 |
| Dehydroascorbate | −8.2294 | 2.32E−11 | 10.635 | 2.07E−09 |
| Cadaverine | −8.1215 | 1.21E−10 | 9.9161 | 8.69E−09 |
| L-aspartate | −7.5675 | 3.73E−10 | 9.4289 | 2.22E−08 |
| D-myo-Inositol 1-2-cyclic phosphate | −7.4525 | 5.85E−10 | 9.2331 | 2.99E−08 |
| Glucosinolate | −6.735 | 6.33E−09 | 8.1987 | 2.83E−07 |
| 5-Hydroxyisourate | −6.2342 | 4.46E−08 | 7.3504 | 1.78E−06 |
| N-Methylethanolamine phosphate | −5.852 | 1.98E−07 | 6.7026 | 7.10E−06 |
| Deoxyribose triphosphate | −5.6167 | 5.32E−07 | 6.2739 | 1.73E−05 |
| L-cystine | −5.5161 | 9.97E−07 | 6.0015 | 2.97E−05 |
| Theogallin | 5.528 | 2.15E−06 | 5.6666 | 5.93E−05 |
| Succinate | −5.1453 | 2.91E−06 | 5.5355 | 7.45E−05 |
| gamma-L-Glutamyl-L-cysteine | −5.1852 | 3.33E−06 | 5.4772 | 7.95E−05 |
| 3-Sulfino-L-alanine | −4.8079 | 1.02E−05 | 4.9897 | 0.0002291 |
| Citrate | −4.7533 | 1.25E−05 | 4.9023 | 0.00026369 |
| 2-acyl-sn-glycero-3-phosphoethanolamine | −4.4796 | 3.48E−05 | 4.4581 | 0.0006926 |
| L-1-Pyrroline-3-hydroxy-5-carboxylate | 4.6005 | 4.80E−05 | 4.3186 | 0.00090481 |
| Homomethionine | −4.3687 | 6.42E−05 | 4.1927 | 0.0011487 |
| Carnosine | −4.1976 | 9.60E−05 | 4.0176 | 0.0016369 |
| alhpa-tocopheronolactone | 4.3296 | 0.00013729 | 3.8624 | 0.0021208 |
| L-cysteine | −4.0662 | 0.00014167 | 3.8487 | 0.0021208 |
| Bilirubin | 4.1129 | 0.00014218 | 3.8472 | 0.0021208 |
| S-Allantoin | 4.0531 | 0.00015481 | 3.8102 | 0.0022169 |
| L-Adrenaline | −3.9747 | 0.00021125 | 3.6752 | 0.0029088 |
| Indole | −3.8512 | 0.00028111 | 3.5511 | 0.0037273 |
| N-Acetylneuraminate | 3.8837 | 0.00038504 | 3.4145 | 0.0049231 |
| Ornithine | 3.6179 | 0.00060238 | 3.2201 | 0.0074362 |
| L-glutamate | 3.7303 | 0.00068926 | 3.1616 | 0.0082252 |
| 1_2-di-9Z_12Z-octadecadienoyl-sn-glycero-3-phosphoserine | 3.5732 | 0.00078078 | 3.1075 | 0.0090168 |
| 2-Methylmaleate | −3.5332 | 0.00080785 | 3.0927 | 0.0090378 |
| 2-Oxoglutarate | −3.291 | 0.0017292 | 2.7621 | 0.018302 |
| gamma-L-Glutamyl-D-alanine | 3.4094 | 0.0017381 | 2.7599 | 0.018302 |
| Biliverdin | 3.1831 | 0.0023522 | 2.6285 | 0.02406 |
| L-glutamine | −3.1111 | 0.0028604 | 2.5436 | 0.028445 |
| Eicosatetraenoic acid | 3.104 | 0.0029523 | 2.5298 | 0.028566 |
| gamma-Glutamyl-Se-methylselenocysteine | −3.0324 | 0.0035398 | 2.451 | 0.033349 |
| epsilon-Caprolactam | 3.064 | 0.0044905 | 2.3477 | 0.04122 |
| ADP | −2.9593 | 0.005451 | 2.2635 | 0.048786 |
| Octylamine | 2.8827 | 0.0061753 | 2.2093 | 0.053921 |
| 2-3-Dinor-8-iso prostaglandin F2alpha | 2.8838 | 0.0067853 | 2.1684 | 0.057836 |
| Indole-3-acetaldehyde | −2.8184 | 0.0074332 | 2.1288 | 0.061886 |
| acyl-C204 | 2.8057 | 0.0078039 | 2.1077 | 0.063495 |
| N-Amidino-L-aspartate | 2.7333 | 0.0081609 | 2.0883 | 0.064925 |
| Taurine | −2.7162 | 0.0089402 | 2.0487 | 0.067917 |
| acyl-C182 | 2.7359 | 0.0090578 | 2.043 | 0.067917 |
| 3-5-Dinitrosalicylic acid | −2.7096 | 0.0091063 | 2.0407 | 0.067917 |
| 5-L-Glutamyl-L-glutamine | 2.7476 | 0.0095621 | 2.0194 | 0.068756 |
| 1-octadecanoyl-sn-glycero-3-phosphoethanolamine | 2.7047 | 0.0096028 | 2.0176 | 0.068756 |
| L-Erythrulose | −2.6403 | 0.010466 | 1.9802 | 0.073469 |
| Nomega-Nomega-Dimethyl-L-arginine | 2.6827 | 0.011202 | 1.9507 | 0.07712 |
| 12-Deoxyaklanonic acid | 2.6206 | 0.011587 | 1.936 | 0.078267 |
| N-Tetradecanoyl-ethanolamine | 2.6017 | 0.011807 | 1.9278 | 0.078279 |
| g-Oxalo-crotonate | 2.5435 | 0.013895 | 1.8571 | 0.090444 |
| Spermidine | −2.5241 | 0.015848 | 1.8 | 0.10076 |
| Mannitol | −2.5455 | 0.016043 | 1.7947 | 0.10076 |
| 2-Aminomuconate | −2.439 | 0.018212 | 1.7396 | 0.11241 |
| 1_2-ditetradecanoyl-sn-glycero-3-phospho-N-methylethanolamine | −2.42 | 0.01917 | 1.7174 | 0.11632 |
| Cys-Gly | −2.3981 | 0.01973 | 1.7049 | 0.11772 |
| Prostaglandin G2 | 2.4092 | 0.021974 | 1.6581 | 0.12896 |
| Chloral hydrate | 2.3035 | 0.025488 | 1.5937 | 0.14717 |
| Sphingosine | 2.2752 | 0.026653 | 1.5743 | 0.15146 |
| 2-5-Dichloro-4-oxohex-2-enedioate | 2.2549 | 0.027974 | 1.5533 | 0.15648 |
| trihydroxy-octadecenoic acid | 2.2744 | 0.029982 | 1.5231 | 0.16508 |
| Serotonin | −2.2456 | 0.031044 | 1.508 | 0.16508 |
| Deethylatrazine | −2.2053 | 0.03138 | 1.5033 | 0.16508 |
| 5-Oxoproline | −2.1971 | 0.032035 | 1.4944 | 0.16508 |
| Poly-gamma-D-glutamate | −2.1971 | 0.032035 | 1.4944 | 0.16508 |
| N-13Z-docosanoyl-ethanolamine | 2.1903 | 0.032278 | 1.4911 | 0.16508 |
| 2-tetradecanoyl-sn-glycero-3-phosphocholine | 2.2013 | 0.033166 | 1.4793 | 0.16723 |
| Hypoxanthine | 2.1696 | 0.03538 | 1.4512 | 0.17516 |
| Epiandrosterone | 2.148 | 0.035717 | 1.4471 | 0.17516 |
| Mercaptopyruvate | −2.1155 | 0.038564 | 1.4138 | 0.18657 |
| L-Noradrenaline | −2.108 | 0.042463 | 1.372 | 0.20269 |
| Trihomomethionine | 2.0499 | 0.044694 | 1.3498 | 0.21053 |
| Guanidinoacetate | 2.0447 | 0.04585 | 1.3387 | 0.21309 |
| 4-Chloroacetanilide | −2.0389 | 0.04648 | 1.3327 | 0.21309 |
| N-9Z_12Z-octadecadienoyl-ethanolamine | 2.0522 | 0.047429 | 1.324 | 0.21309 |
| 2--7-Dihydroxy-4--5--methylene-dioxyisoflavone | 2.0621 | 0.047618 | 1.3222 | 0.21309 |
| L-Cysteate | 2.0149 | 0.049033 | 1.3095 | 0.21672 |

REFERENCES

Barallobre-Barreiro J, Chung Y-L, Mayr M (2013). Proteomics and Metabolomics for Mechanistic Insights and Biomarker Discovery in Cardiovascular Disease. *Revista Española de Cardiología* (English Edition). 66, 657-661.

Belsky D W, Caspi A, Houts R, Cohen H J, Corcoran D L, Danese A, Harrington H, Israel S, Levine M E, Schaefer J D, Sugden K, Williams B, Yashin A I, Poulton R, Moffitt T E (2015). Quantification of biological aging in young adults. *Proc Natl Acad Sci USA*. 112, E4104-4110.

Blair S N, Kohl H, Paffenbarger R S, Clark D G, Cooper K H, Gibbons L W (1989). Physical fitness and all-cause mortality. *Jama*. 262, 2395-2401.

Bradshaw D I, George J D, Hyde A, LaMonte M J, Vehrs P R, Hager R L, Yanowitz F G (2005). An accurate VO2max nonexercise regression model for 18-65-year-old adults. *Research quarterly for exercise and sport*. 76, 426-432.

Brooks-Wilson A R (2013). Genetics of healthy aging and longevity. *Hum Genet*. 132, 1323-1338.

Calle E E, Thun M J, Petrelli J M, Rodriguez C, Heath C W, Jr. (1999). Body-mass index and mortality in a prospective cohort of U.S. adults. *N Engl J Med*. 341, 1097-1105.

Cao Z-B, Miyatake N, Higuchi M, Miyachi M, Ishikawa-Takata K, Tabata I (2010). Predicting V̇O$_2$max with an objectively measured physical activity in Japanese women. *Medicine & Science in Sports & Exercise*. 42, 179-186.

Cho I H, Park K S, Lim C J (2010). An empirical comparative study on biological age estimation algorithms with an application of Work Ability Index (WAI). *Mech Ageing Dev.* 131, 69-78.

Clasquin M F, Melamud E, Rabinowitz J D (2012). L C-M S data processing with MAVEN: a metabolomic analysis and visualization engine. *Curr Protoc Bioinformatics.* Chapter 14, Unit 14 11.

Finkel T (2015). The metabolic regulation of aging. *Nature medicine.* 21, 1416-1423.

Fleg J L, Morrell C H, Bos A G, Brant L J, Talbot L A, Wright J G, Lakatta E G (2005). Accelerated longitudinal decline of aerobic capacity in healthy older adults. *Circulation.* 112, 674-682.

Franceschi C, Campisi J (2014). Chronic inflammation (inflammaging) and its potential contribution to age-associated diseases. *J Gerontol A Biol Sci Med Sci.* 69 Suppl 1, S4-9.

Hannum G, Guinney J, Zhao L, Zhang L, Hughes G, Sadda S, Klotzle B, Bibikova M, Fan J B, Gao Y, Deconde R, Chen M, Rajapakse I, Friend S, Ideker T, Zhang K (2013). Genome-wide methylation profiles reveal quantitative views of human aging rates. *Mol Cell.* 49, 359-367.

Hardie D G, Ross F A, Hawley S A (2012). AMPK: a nutrient and energy sensor that maintains energy homeostasis. *Nat Rev Mol Cell Biol.* 13, 251-262.

Hasek B E, Stewart L K, Henagan T M, Boudreau A, Lenard N R, Black C, Shin J, Huypens P, Malloy V L, Plaisance E P, Krajcik R A, Orentreich N, Gettys T W (2010). Dietary methionine restriction enhances metabolic flexibility and increases uncoupled respiration in both fed and fasted states. *Am J Physiol Regul Integr Comp Physiol.* 299, R728-739.

Horvath S (2013). DNA methylation age of human tissues and cell types. *Genome Biol.* 14, R115.

Houtkooper R H, Argmann C, Houten S M, Canto C, Jeninga E H, Andreux P A, Thomas C, Doenlen R, Schoonjans K, Auwerx J (2011). The metabolic footprint of aging in mice. *Sci Rep.* 1, 134.

Houtkooper R H, Williams R W, Auwerx J (2010). Metabolic networks of longevity. *Cell.* 142, 9-14.

Jackson A S, Blair S N, Mahar M T, Wier L T, Ross R M, Stuteville J E (1990). Prediction of functional aerobic capacity without exercise testing. *Med Sci Sports Exerc.* 22, 863-870.

Jiang T, Yu J-T, Tian Y, Tan L (2013). Epidemiology and etiology of Alzheimer's disease: from genetic to non-genetic factors. *Current Alzheimer Research.* 10, 852-867.

Kennedy B K, Berger S L, Brunet A, Campisi J, Cuervo A M, Epel E S, Franceschi C, Lithgow G J, Morimoto R I, Pessin J E, Rando T A, Richardson A, Schadt E E, Wyss-Coray T, Sierra F (2014). Geroscience: linking aging to chronic disease. *Cell.* 159, 709-713.

Kim S, Myers L, Wyckoff J, Cherry K E, Jazwinski S M (2017). The frailty index outperforms DNA methylation age and its derivatives as an indicator of biological age. *Geroscience.* 39, 83-92.

Klemera P, Doubal S (2006). A new approach to the concept and computation of biological age. *Mech Ageing Dev.* 127, 240-248.

Koves T R, Ussher J R, Noland R C, Slentz D, Mosedale M, Ilkayeva O, Bain J, Stevens R, Dyck J R, Newgard C B, Lopaschuk G D, Muoio D M (2008). Mitochondrial overload and incomplete fatty acid oxidation contribute to skeletal muscle insulin resistance. *Cell Metab.* 7, 45-56.

Kujoth G C, Hiona A, Pugh T D, Someya S, Panzer K, Wohlgemuth S E, Hofer T, Seo A Y, Sullivan R, Jobling W A, Morrow J D, Van Remmen H, Sedivy J M, Yamasoba T, Tanokura M, Weindruch R, Leeuwenburgh C, Prolla T A (2005). Mitochondrial DNA mutations, oxidative stress, and apoptosis in mammalian aging. *Science.* 309, 481-484.

Laukkanen J A, Kurl S, Salonen R, Rauramaa R, Salonen J T (2004). The predictive value of cardiorespiratory fitness for cardiovascular events in men with various risk profiles: a prospective population-based cohort study. *European heart journal.* 25, 1428-1437.

Lawton K A, Berger A, Mitchell M, Milgram K E, Evans A M, Guo L, Hanson R W, Kalhan S C, Ryals J A, Milburn M V (2008). Analysis of the adult human plasma metabolome. *Pharmacogenomics.* 9, 383-397.

Levine M E (2013). Modeling the rate of senescence: can estimated biological age predict mortality more accurately than chronological age? *J Gerontol A Biol Sci Med Sci.* 68, 667-674.

Lopez-Otin C, Blasco M A, Partridge L, Serrano M, Kroemer G (2013). The hallmarks of aging. *Cell.* 153, 1194-1217.

López-Otín C, Galluzzi L, Freije J M, Madeo F, Kroemer G (2016). Metabolic control of longevity. *Cell.* 166, 802-821.

Lunenfeld B, Stratton P (2013). The clinical consequences of an ageing world and preventive strategies. *Best Pract Res Clin Obstet Gynaecol.* 27, 643-659.

Mapstone M, Cheema A K, Fiandaca M S, Zhong X, Mhyre T R, MacArthur L H, Hall W J, Fisher S G, Peterson D R, Haley J M (2014). Plasma phospholipids identify antecedent memory impairment in older adults. *Nature medicine.*

Mitnitski A, Song X, Rockwood K (2013). Assessing biological aging: the origin of deficit accumulation. *Biogerontology.* 14, 709-717.

Nakamura E (1991). A study on the basic nature of human biological aging processes based upon a hierarchical factor solution of the age-related physiological variables. *Mech Ageing Dev.* 60, 153-170.

Nemkov T, Hansen K C, D'Alessandro A (2017). A three-minute method for high-throughput quantitative metabolomics and quantitative tracing experiments of central carbon and nitrogen pathways. *Rapid Commun Mass Spectrom.* 31, 663-673.

Nes B M, Janszky I, Vatten L J, Nilsen T, Aspenes S T, Wisloff U (2011). Estimating VO 2peak from a nonexercise prediction model: the HUNT Study, Norway. *Med Sci Sports Exerc.* 43, 2024-2030.

Noland R C, Koves T R, Seiler S E, Lum H, Lust R M, Ilkayeva O, Stevens R D, Hegardt F G, Muoio D M (2009). Carnitine insufficiency caused by aging and overnutrition compromises mitochondrial performance and metabolic control. *Journal of Biological Chemistry.* 284, 22840-22852.

Ross R, Blair S N, Arena R, Church T S, Despres J P, Franklin B A, Haskell W L, Kaminsky L A, Levine B D, Lavie C J, Myers J, Niebauer J, Sallis R, Sawada S S, Sui X, Wisloff U, American Heart Association Physical Activity Committee of the Council on L, Cardiometabolic H, Council on Clinical C, Council on E, Prevention, Council on C, Stroke N, Council on Functional G, Translational B, Stroke C (2016). Importance of Assessing Cardiorespiratory Fitness in Clinical Practice: A Case for Fitness as a Clinical Vital Sign: A Scientific Statement From the American Heart Association. *Circulation.* 134, e653-e699.

Sebastiani P, Thyagarajan B, Sun F, Schupf N, Newman A B, Montano M, Perls T T (2017). Biomarker signatures of aging. *Aging cell.* 16, 329-338.

Soltow Q A, Jones D P, Promislow D E (2010). A network perspective on metabolism and aging. *Integrative and comparative biology.* 50, 844-854.

Sui X, LaMonte M J, Blair S N (2007). Cardiorespiratory fitness as a predictor of nonfatal cardiovascular events in asymptomatic women and men. *American journal of epidemiology.* 165, 1413-1423.

Sun L, Sadighi Akha A A, Miller R A, Harper J M (2009). Life-span extension in mice by preweaning food restriction and by methionine restriction in middle age. *J Gerontol A Biol Sci Med Sci.* 64, 711-722.

Verdin E (2015). NAD(+) in aging, metabolism, and neurodegeneration. *Science.* 350, 1208-1213.

Wang Y, Hekimi S (2015). Mitochondrial dysfunction and longevity in animals: Untangling the knot. *Science.* 350, 1204-1207.

Wells J C (2007). Sexual dimorphism of body composition. *Best Pract Res Clin Endocrinol Metab.* 21, 415-430.

Wiley C D, Velarde M C, Lecot P, Liu S, Sarnoski E A, Freund A, Shirakawa K, Lim H W, Davis S S, Ramanathan A, Gerencser A A, Verdin E, Campisi J (2016). Mitochondrial Dysfunction Induces Senescence with a Distinct Secretory Phenotype. *Cell Metab.* 23, 303-314.

Xia J, Wishart D S (2016). Using MetaboAnalyst 3.0 for Comprehensive Metabolomics Data Analysis. *Curr Protoc Bioinformatics.* 55, 14 10 11-14 10 91.

Glossary of Claim Terms

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The invention pertains, at least in part, to the generation of small molecule profiles of samples, cells, and cellular compartments. Small molecule profiles "fingerprint" the cell or cellular compartment and identify the presence, absence or relative quantity of small molecules. The small molecule profiles of the cells or cellular compartments may be obtained through, for example, a single technique or a combination of techniques for separating and/or identifying small molecules known in the art. Examples of separation and analytical techniques which can be used to separate and identify the compounds of the small molecule profiles include: HPLC, TLC, electrochemical analysis, mass spectroscopy, refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS) and other methods known in the art.

The term "small molecules" includes organic and inorganic molecules which are present in the cell, cellular compartment, organelle or extracellular space. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell. In one embodiment, the small molecules of the invention are isolated.

The term "metabolome" includes all of the small molecules present in a given organism. The metabolome includes both metabolites as well as products of catabolism.

The term "metabolomic marker" refers to a molecule selected by a comparison of small molecule profiles wherein the molecule is observed to increase or decrease responsive to the application of a stimuli.

The language "small molecule profile" includes the inventory of small molecules in tangible form within a targeted cell, extracellular space, tissue, organ, organism, or any derivative fraction thereof, e.g., cellular compartment, that is necessary and/or sufficient to provide information to a user for its intended use within the methods described herein. The inventory would include the quantity and/or type of small molecules present. The ordinarily skilled artisan would know that the information which is necessary and/or sufficient will vary depending on the intended use of the "small molecule profile." For example, the "small molecule profile," " can be determined using a single technique for an intended use but may require the use of several different techniques for another intended use depending on such factors as the disease state involved, the types of small molecules present in a particular targeted cellular compartment, the cellular compartment being assayed per se., etc.

The relevant information in a "small molecule profile" also may vary depending on the intended use of the compiled information, e.g. spectra. For example for some intended uses, the amounts of a particular small molecule or a particular class of small molecules may be relevant, but for other uses the distribution of types of small molecules may be relevant.

The ordinarily skilled artisan would be able to determine the appropriate "small molecule profiles" for each method described herein by comparing small molecule profiles from diseased and/or test subjects with standard and/or healthy subjects. These comparisons can be made by individuals, e.g., visually, or can be made using software designed to make such comparisons, e.g., a software program may provide a secondary output which provides useful information to a user. For example, a software program can be used to confirm a profile or can be used to provide a read-out when a comparison between profiles is not possible with a "naked eye". The selection of an appropriate software program, e.g., a pattern recognition software program, is within the ordinary skill of the art. It should be noted that the comparison of the profiles can be done both quantitatively and qualitatively.

In certain embodiments, the invention includes a method of identifying disease-relevant small molecules. The method includes comparing changes in small molecule profiles of diseased cells, cellular compartments, extracellular spaces or organelles, both pre- and post-initiation of treatment to a standard profile or to a standard set of predetermined metabolomic markers. The method also involves identifying the small molecules which are present in aberrant amounts in the diseased small molecule profile. The small molecules present in aberrant amounts in the diseased cells are "disease-relevant small molecules."

The language "disease-relevant small molecules" includes both small molecules present in aberrant amount in diseased small molecule profiles and, in addition, small molecules which are potentially involved in disease initiation, progression or prediction. The language "aberrant levels" includes any level, amount, or concentration of a small molecule in a cell, cellular compartment, extracellular space or organelle which is different from the level of the small molecule of a standard sample.

The term "standard profile" includes profiles derived from healthy cells, advantageously from a similar origin as the source. In one embodiment, the standard profile is an average of many samples of a certain cell type and/or a certain cellular compartment. In another embodiment, the standard profile may be derived from a patient prior to the onset of the disease state or from cells not affected by the disease state. Or, in another embodiment the standard profile can be an average of the profiles obtained from numerous sources, e.g., the standard profile may be an average of small molecule profiles obtained from 2 or more subjects. The standard profile can be a small molecule profile of a certain cellular compartment or from a certain subset of cells. Advantageously, the small molecules with aberrant levels in the sample are identified, e.g., HPLC, TLC, electrochemical analysis, mass spectroscopy, refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), Light Scattering analysis (LS) and other methods known in the art. In one embodiment, the small molecule profile of the sample, cell, or cellular compartment, is compared to the standard profile by using subtracting one profile from the other. Standard profiles can also be made of the effects of certain agents (e.g., drugs, therapeutic agents, toxins, etc.) on both healthy and diseased cells (e.g., cells diseased with the type of disease treated by the therapeutic agent).

The term "about" or "approximately" as used herein means within 20%, preferably within 10%, and more preferably within 5% of a given value or range.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "subject" preferably refers to a human, such as a human being screened for metabolomic markers indicative of biological age, and more preferably a human in need screening for an age-related disease or condition. However, the term "subject" can also refer to non-human animals, preferably mammals such as dogs, cats, horses, cows, pigs, sheep and non-human primates, among others, that are in need of screening for biological age.

As used herein, "treating" means treating or ameliorating, and treating or ameliorating means the reduction or complete removal of one or more symptoms of a disease or medical condition, such as age-related diseases or conditions (e.g. administering therapeutics such as drugs for elevated glucose or cholesterol profiles). Such treatment or amelioration can include the delay or elimination of the onset of one or more symptoms when administered to a person at risk for the disease or medical condition. Tests for the success of treatment or amelioration are well known in the art.

The "level" of one or more biomarkers means the absolute or relative amount or concentration of the biomarker in the sample.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, blood, blood plasma, urine, cerebral spinal fluid (CSF), crevicular fluid, saliva or breath condensate.

A "reference level" of a biomarker means a level of the biomarker that is indicative of a particular age, particular age range, disease state, phenotype, or lack thereof, as well as combinations of disease states, phenotypes, or lack thereof. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular metabolic ages, age ranges, disease or illness state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Reference levels may also tailored to specific populations of subjects, including gender populations, race populations, or combinations thereof (e.g. white males, white females, Asian males, Asian females, Hispanic males, or Hispanic females). Such reference levels may also be tailored to specific techniques that are used to measure levels of biomarkers in biological samples (e.g., LC-MS, GC-MS, etc.), where the levels of biomarkers may differ based on the specific technique that is used.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for assaying a plurality of biomarkers, wherein the method comprises:
    obtaining a physiological sample from a subject; and
    measuring in the physiological sample a set of biomarkers, wherein the set of biomarkers comprises (i) Oxaloacetate and Acyl-C5-OH, and (ii) 2-Phospho-D-Glycerate, Ascorbate, Selenohomocystine, 5-Acetylamino-6-formylamino-3-methyluracil, Phosphate, and Octylamine, to produce test data comprising a plurality of biomarker measures.

* * * * *